(12) United States Patent
Eckelt et al.

(10) Patent No.: US 9,429,520 B2
(45) Date of Patent: Aug. 30, 2016

(54) ENRICHMENT AND IDENTIFICATION OF FETAL CELLS IN MATERNAL BLOOD AND LIGANDS FOR SUCH USE

(75) Inventors: Andreas Eckelt, Odenthal (DE); Britta Christensen, Birkerød (DK); Steen Kolvraa, Skødstrup (DK); Marie Brinch, Vejle (DK); Ripudaman Singh, Århus C (DK); Lotte Hatt, Skanderborg (DK)

(73) Assignee: Arcedi Biotech ApS, Vejle (DK)

(*) Notice: Subject to any disclaimer, the term of this patent is extended or adjusted under 35 U.S.C. 154(b) by 367 days.

(21) Appl. No.: 13/883,455

(22) PCT Filed: Nov. 9, 2011

(86) PCT No.: PCT/DK2011/050423
§ 371 (c)(1),
(2), (4) Date: Aug. 26, 2013

(87) PCT Pub. No.: WO2012/062325
PCT Pub. Date: May 18, 2012

(65) Prior Publication Data
US 2013/0331284 A1 Dec. 12, 2013

(30) Foreign Application Priority Data
Nov. 9, 2010 (DK) ................. 2010 01018

(51) Int. Cl.
| | | |
|---|---|---|
| *C07H 21/04* | (2006.01) | |
| *C12Q 1/68* | (2006.01) | |
| *G01N 21/64* | (2006.01) | |
| *G01N 33/569* | (2006.01) | |

(52) U.S. Cl.
CPC ......... *G01N 21/6486* (2013.01); *C12Q 1/6811* (2013.01); *C12Q 1/6881* (2013.01); *G01N 33/56966* (2013.01); *C12Q 1/6806* (2013.01); *C12Q 2600/156* (2013.01); *G01N 2333/4742* (2013.01); *G01N 2333/70596* (2013.01)

(58) Field of Classification Search
None
See application file for complete search history.

(56) References Cited

U.S. PATENT DOCUMENTS

| | | | | |
|---|---|---|---|---|
| 5,714,325 A | * | 2/1998 | Bianchi ............... | C12Q 1/6804 435/40.5 |
| 5,861,253 A | | 1/1999 | Asgari et al. | |
| 2003/0148295 A1 | | 8/2003 | Wan et al. | |
| 2007/0015171 A1 | | 1/2007 | Bianchi | |

FOREIGN PATENT DOCUMENTS

| | | |
|---|---|---|
| WO | WO 94/02646 | 2/1994 |
| WO | WO 01/79851 A1 | 10/2001 |
| WO | WO 01/88100 | 11/2001 |
| WO | WO 2008/132753 A2 | 11/2008 |
| WO | WO 2009/103110 A1 | 8/2009 |
| WO | WO 2010/078872 A2 | 7/2010 |
| WO | 2010121315 A1 | 10/2010 |

OTHER PUBLICATIONS

Gotherstrom et al (Mol. Human Reproduction, vol. 16, No. 7, pp. 472-480, Mar. 3, 2010).*
Bianchi et al. (Prenatal Diagnosis, vol. 13, pp. 293-300, 1993).*
Hager et al. (Gynecologic Oncology, vol. 98, pp. 211-216, 2005).*
Carlino et al (Blood, vol. 111, No. 6, pp. 3108-3115, 2008).*
Hemberger et al. (Developmental Dynamics, vol. 227, pp. 185-191, 2003).*
deSouza et al. (Tissue & Cell, vol. 33, No. 1, pp. 40-45, 2001).*
Lipecka, J., et al., "Rescue of ΔF508-CFTR (Cystic Fibrosis Transmembrane Conductance Regulator) by Curcumin: Involvement of the Keratin 18 Network" *The Journal of Pharmacology and Experimental Therapeutics*, 317(2): 500-505 (2006).
Notification of Transmittal of The International Search Report and the Written Opinion for International Application No. PCT/DK2011/050423, Title: "Enrichment and Identification of Fetal Cells in Maternal Blood and Ligands for Such Use," Date of Mailing Mar. 8, 2012, 18 pages.
Vicovac, L. et al., "Epithelial-Masenchymal Transition During Trophoblast Differentiation", ACTA Anatomica, 156(3): 202-216 (1996).
Huie, M.A., et al., "Antibodies to Human Fetal Erythroid Cells From a Nonimmune Phage Antibody Library," *Proceedings of the National Academy of Sciences of USA*, 98(5): 2682-2687 (2001).
Koumantaki, Y., et al., "Microsatellite Analysis Provides Efficient Confirmation of Fetal Trophoblast Isolation From Maternal Circulation," *Prenatal Diagnosis*, 21:566-570 (2001).
Zhou, Y., et al., "Human Cytotrophoblasts Adopt a Vascular Phenotype as They Differentiate," *J. Clin, Invest.*, 99(9):2139-2151 (1997).
Soncini, M., et al., "Isolation and Characterization of Mesenchymal Cells from Human Fetal Membranes", *Journal of Tissue Engineering and Regenerative Medicine*, 1:296-305 (2007).

(Continued)

*Primary Examiner* — Jeanine A Goldberg
(74) *Attorney, Agent, or Firm* — Posternak Blankstein & Lund LLP

(57) ABSTRACT

The present invention relates to enrichment and/or identification of fetal cells of a maternal blood sample using fetal cell specific ligands and/or fetal cell specific hybridization probes wherein the ligand or probes are directed to an endothelial/mesenchymal marker, e.g. CD105, CD146 or CD141, in a first round of enrichment and the ligand or probes, in a second round of enrichment, are directed to an epithelial marker, e.g. a cytokeratin, such as CK7, CK8, CK18 or CK19. Enriched or identified fetal cells may be subjected to steps of detection or diagnosis, wherefore the present invention enables non-invasive 5 prenatal diagnostics.

30 Claims, 6 Drawing Sheets

(56) References Cited

OTHER PUBLICATIONS

Delsol, G., et al., "Antibody BNH Detects Red Blood Cell-Related Antigens on Anaplastic Large Cell CD30+ Positive Lymphomas," *British Journal of Cancer*,64(2):321-326 (1991).

Database Geo [online], Apr. 19, 2010, "Affymetrix Human Genome U133 Plus 2.0 Array", XP002668741, retrieved from NCBI database accession No. GPL9987, abstract.

Kunisakc, S.M., et al., "Fetal Cartilage Engineering from Amniotic Mesenchymal Progenitor Cells," *Stem Cells and Development, Elsevier*, NL, 15(2): 245-253 (2006); XP008100090, ISSN: 1547-3287, DOI: 10.1089/SCD.2006.15.245 abstract.

Davydova, D.A., et al., "Culture of Human Amniotic Fluid Stem Cells in 3D Collagen Matrix," *Cell and Tissue Biology*, 5(4): 339-345 (2011).

Gussin, H.A.E., "Culture of Endothelial Cells Isolated from Maternal Blood Using Anti-CD105 and CD133," *Prenatal Diagnostics*, 24:189-193 (2004).

International Preliminary Report on Patentability for International Application No. PCT/DK2011/050423, Title: "Enrichment and Identification of Fetal Cells in Maternal Blood and Ligands for Such Use," Date of Issuance May 14, 2013, 9 pages.

Kögler, Gesine et al; "A New Human Somatic Stem Cell from Placental Cord Blood with Intrinsic Pluripotent Differentiation Potential"; J. Exped. Med; vol. 200, No. 2, Jul. 19, 2004, pp. 123-135.

Na, Kyu-Hwan et al; "Isolation and Characterization of Trophoblast Stem Cells-like Cells Derived from Human Term Placenta"; Dev. Reprod., vol. 14, No. 3, 2010, pp. 155-162.

\* cited by examiner

SEQUENCE LISTING

<160> NUMBER OF SEQ ID NOS: 13

<210> SEQ ID NO 1
<211> LENGTH: 3072
<212> TYPE: DNA
<213> ORGANISM: Homo sapiens

<400> SEQUENCE: 1

```
ctctacccgg ttggcaggcg gcctggccca gccccttctc taaggaagcg catttcctgc      60
ctccctgggc cggccgggct ggatgagccg ggagctccct gctgccggtc ataccacagc     120
cttcatctgc gccctggggc caggactgct gctgtcactg ccatccattg gagcccagca     180
cccccctccc gcccatcctt cggacagcaa ctccagccca gccccgcgtc cctgtgtcca     240
cttctcctga cccctcggcc gccaccccag aaggctggag cagggacgcc gtcgctccgg     300
ccgcctgctc ccctcgggtc cccgtgcgag cccacgccgg ccccggtgcc cgcccgcagc     360
cctgccactg gacacaggat aaggcccagc gcacaggccc ccacgtggac agcatggacc     420
gcggcacgct ccctctggct gttgccctgc tgctggccag ctgcagcctc agccccacaa     480
gtcttgcaga aacagtccat tgtgaccttc agcctgtggg ccccgagagg ggcgaggtga     540
catataccac tagccaggtc tcgaagggct gcgtggctca ggcccccaat gccatccttg     600
aagtccatgt cctcttcctg gagttcccaa cgggcccgtc acagctggag ctgactctcc     660
aggcatccaa gcaaaatggc acctggcccc gagaggtgct tctggtcctc agtgtaaaca     720
gcagtgtctt cctgcatctc caggccctgg gaatcccact gcacttggcc tacaattcca     780
gcctggtcac cttccaagag ccccggggg tcaacaccac agagctgcca tccttcccca     840
agacccagat ccttgagtgg gcagctgaga ggggcccat cacctctgct gctgagctga     900
atgacccca gagcatcctc ctccgactgg gccaagccca ggggtcactg tccttctgca     960
tgctggaagc cagccaggac atgggccgca cgctcgagtg gcggccgcgt actccagcct    1020
tggtccgggg ctgccacttg gaaggcgtgg ccggccacaa ggaggcgcac atcctgaggg    1080
tcctgccggg ccactcggcc gggccccgga cggtgacggt gaaggtggaa ctgagctgcg    1140
cacccgggga tctcgatgcc gtcctcatcc tgcagggtcc ccctacgtg tcctggctca    1200
tcgacgccaa ccacaacatg cagatctgga ccactggaga atactccttc aagatctttc    1260
cagagaaaaa cattcgtggc ttcaagctcc cagacacacc tcaaggcctc ctgggggagg    1320
cccggatgct caatgccagc attgtggcat ccttcgtgga gctaccgctg ccagcattg    1380
tctcacttca tgcctccagc tgcggtggta ggctgcagac ctcacccgca ccgatccaga    1440
ccactcctcc caaggacact tgtagcccgg agctgctcat gtccttgatc cagacaaagt    1500
gtgccgacga cgccatgacc ctggtactaa agaaagagct tgttgcgcat ttgaagtgca    1560
ccatcacggg cctgaccttc tgggacccca gctgtgaggc agaggacagg ggtgacaagt    1620
ttgtcttgcg cagtgcttac tccagctgtg gcatgcaggt gtcagcaagt atgatcagca    1680
atgaggcggt ggtcaatatc ctgtcgagct catcaccaca gcggaaaaag gtgcactgcc    1740
tcaacatgga cagcctctct ttccagctgg gcctctacct cagcccacac ttcctccagg    1800
cctccaacac catcgagccg gggcagcaga gctttgtgca ggtcagagtg tccccatccg    1860
tctccgagtt cctgctccag ttagacagct gccacctgga cttggggcct gagggaggca    1920
ccgtggaact catccagggc cgggcggcca agggcaactg tgtgagcctg ctgtccccaa    1980
gccccgaggg tgacccgcgc ttcagcttcc tcctccactt ctacacagta cccatacca    2040
aaaccggcac cctcagctgc acggtagccc tgcgtcccaa gaccgggtct caagaccagg    2100
aagtccatag gactgtcttc atgcgcttga acatcatcag ccctgacctg tctggttgca    2160
caagcaaagg cctcgtcctg ccgccgtgc tgggcatcac cttggtgcc ttcctcatcg    2220
gggccctgct cactgctgca ctctggtaca tctactcgca cacgcgttcc cccagcaagc    2280
gggagcccgt ggtggcggtg gctgcccgg cctcctcgga gagcagcagc accaaccaca    2340
```

```
gcatcgggag cacccagagc acccctgct ccaccagcag catggcatag ccccggcccc    2400
ccgcgctcgc ccagcaggag agactgagca gccgccagct gggagcactg gtgtgaactc    2460
accctgggag ccagtcctcc actcgaccca gaatggagcc tgctctccgc gcctaccctt    2520
cccgcctccc tctcagaggc ctgctgccag tgcagccact ggcttggaac accttggggt    2580
ccctccaccc cacagaacct tcaacccagt gggtctggga tatggctgcc aggagacag     2640
accacttgcc acgctgttgt aaaaacccaa gtccctgtca tttgaacctg gatcagcac     2700
tggtgaactg agctgggcag aagggagaa cttgaaacag attcaggcca gcccagccag     2760
gccaacagca cctccccgct gggaagagaa gagggcccag cccagagcca cctggatcta    2820
tccctgcggc ctccacacct gaacttgcct aactaactgg caggggagac aggagcctag    2880
cggagcccag cctgggagcc cagagggtgg caagaacagt gggcgttggg agcctagctc    2940
ctgccacatg gagccccctc tgccggtcgg gcagccagca gaggggagt agccaagctg     3000
cttgtcctgg gcctgcccct gtgtattcac caccaataaa tcagaccatg aaaccagtga    3060
aaaaaaaaa aa                                                         3072
```

<210> SEQ ID NO 2
<211> LENGTH: 3196
<212> TYPE: DNA
<213> ORGANISM: Homo sapiens

<400> SEQUENCE: 2

```
ctctacccgg ttggcaggcg gcctggccca gcccttctc taaggaagcg catttcctgc     60
ctccctgggc cggccgggct ggatgagccg ggagctccct gctgccggtc ataccacagc    120
cttcatctgc gccctggggc caggactgct gctgtcactg ccatccattg gagcccagca    180
ccccctcccc gcccatcctt cggacagcaa ctccagccca gccccgcgtc cctgtgtcca    240
cttctcctga cccctcggcc gccaccccag aaggctggag cagggacgcc gtcgctccgg    300
ccgcctgctc ccctcgggtc ccgtgcgag cccacgccgg ccccggtgcc cgcccgcagc     360
cctgccactg acacaggat aaggcccagc gcacaggccc ccacgtggac agcatggacc     420
gcggcacgct ccctctggct gttgcccctgc tgctggccag ctgcagcctc agccccacaa    480
gtcttgcaga acagtccat tgtgaccttc agcctgtggg cccgagagg ggcgaggtga     540
catataccac tagccaggtc tcgaagggct gcgtggctca ggcccccaat gccatccttg    600
aagtccatgt cctcttcctg gagttcccaa cgggcccgtc acagctggag ctgactctcc    660
aggcatccaa gcaaaatggc acctggcccc gagaggtgct tctggtcctc agtgtaaaca    720
gcagtgtctt cctgcatctc caggccctgg gaatcccact gcacttggcc tacaattcca    780
gcctggtcac cttccaagag cccccggggg tcaacaccac agagctgcca tccttcccca    840
agacccagat ccttgagtgg gcagctgaga ggggccccat cacctctgct gctgagctga    900
atgaccccca gagcatcctc ctccgactgg gccaagccca gggtcactg tccttctgca    960
tgctggaagc cagccaggac atgggccgca cgctcgagtg gcggccgcgt actccagcct   1020
tggtccgggg ctgccacttg aaggcgtgg ccggccacaa ggaggcgcac atcctgaggg    1080
tcctgccggg ccactcggcc gggccccgga cggtgacggt gaaggtggaa ctgagctgcg   1140
caccgggga tctcgatgcc gtcctcatcc tgcagggtcc ccctacgtg tcctggctca    1200
tcgacgccaa ccacaacatg cagatctgga ccactggaga atactccttc aagatctttc   1260
cagagaaaaa cattcgtggc ttcaagctcc cagacacacc tcaaggcctc ctgggggagg   1320
cccggatgct caatgccagc attgtggcat ccttcgtgga gctaccgctg ccagcattg    1380
```

```
tctcacttca tgcctccagc tgcggtggta ggctgcagac ctcacccgca ccgatccaga    1440
ccactcctcc caaggacact tgtagcccgg agctgctcat gtccttgatc cagacaaagt    1500
gtgccgacga cgccatgacc ctggtactaa agaaagagct tgttgcgcat ttgaagtgca    1560
ccatcacggg cctgaccttc tgggacccca gctgtgaggc agaggacagg ggtgacaagt    1620
ttgtcttgcg cagtgcttac tccagctgtg gcatgcaggt gtcagcaagt atgatcagca    1680
atgaggcggt ggtcaatatc ctgtcgagct catcaccaca gcggaaaaag gtgcactgcc    1740
tcaacatgga cagcctctct ttccagctgg gcctctacct cagcccacac ttcctccagg    1800
cctccaacac catcgagccg ggcagcagag gctttgtgca ggtcagagtg tccccatccg    1860
tctccgagtt cctgctccag ttagacagct gccacctgga cttggggcct gagggaggca    1920
ccgtggaact catccagggc cgggcggcca agggcaactg tgtgagcctg ctgtccccaa    1980
gccccgaggg tgacccgcgc ttcagcttcc tcctccactt ctacacagta cccataccca    2040
aaaccggcac cctcagctgc acggtagccc tgcgtcccaa gaccgggtct caagaccagg    2100
aagtccatag gactgtcttc atgcgcttga acatcatcag ccctgacctg tctggttgca    2160
caagcaaagg cctcgtcctg cccgccgtgc tgggcatcac cttggtgcc ttcctcatcg    2220 gggccctgct cactgctgca ctctggtaca tctactcgca cacgcgtgag taccccaggc    2280
ccccacagtg agcatgccgg gcccctccat ccacccgggg gagcccagtg aagcctctga    2340
gggattgagg ggccctggcc aggaccctga cctccgcccc tgccccgct cccgctccca    2400 ggttccccca gcaagcggga gcccgtggtg gcggtggctg ccccggcctc ctcggagagc    2460
agcagcacca accacagcat cgggagcacc cagagcaccc cctgctccac cagcagcatg    2520
gcatagcccc ggccccccgc gctcgcccag caggagagac tgagcagccg ccagctggga    2580
gcactggtgt gaactcaccc tgggagccag tcctccactc gacccagaat ggagcctgct    2640
ctccgcgcct acccttcccg cctccctctc agaggcctgc tgccagtgca gccactggct    2700
tggaacacct tggggtccct ccaccccaca gaaccttcaa cccagtgggt ctgggatatg    2760 gctgccagg agacagacca cttgccacgc tgttgtaaaa acccaagtcc ctgtcatttg    2820
aacctggatc cagcactggt gaactgagct gggcaggaag ggagaacttg aaacagattc    2880
aggccagccc agccaggcca acagcacctc cccgctggga agagaagagg gcccagccca    2940
gagccacctg gatctatccc tgcggcctcc acacctgaac ttgcctaact aactggcagg    3000
ggagacagga gcctagcgga gcccagcctg ggagcccaga gggtggcaag aacagtgggc    3060
gttgggagcc tagctcctgc cacatggagc cccctctgcc ggtcgggcag ccagcagagg    3120
gggagtagcc aagctgcttg tcctgggcct gcccctgtgt attcaccacc aataaatcag    3180
accatgaaac cagtga                                                   3196
```

<210> SEQ ID NO 3
<211> LENGTH: 2147
<212> TYPE: DNA
<213> ORGANISM: Homo sapiens

<400> SEQUENCE: 3

```
actcaccggc ctgggccctg tcacttctct gatagctccc agctcgctct ctgcagccat      60
gattgccaga cagcagtgtg tccgaggcgg gccccggggc ttcagctgtg gctcggccat     120
tgtaggcggt ggcaagagag gtgccttcag ctcagtctcc atgtctggag gtgctggccg     180
atgctcttct gggggatttg gcagcagaag cctctacaac ctcaggggga acaaaagcat     240
```

```
ctccatgagt gtggctgggt cacgacaagg tgcctgcttt gggggtgctg gaggctttgg      300
cactggtggc tttggtggtg gatttggggg ctccttcagt ggtaagggtg ccctggctt       360 ccccgtctgc cccgctgggg gaattcagga ggtcaccatc aaccagagct tgctcacccc      420
cctccacgtg gagattgacc ctgagatcca gaaagtccgg acggaagagc gcaacagat      480 caagctcctc aacaacaagt tgcctcctt catcgacaag gtgcagttct tagagcaaca      540
gaataaggtc ctggagacca aatggaacct gctccagcag cagacgacca ccacctccag      600
caaaaacctt gagcccctct tgagaccta cctcagtgtc ctgaggaagc agctagatac       660
cttgggcaat gacaaagggc gcctgcagtc tgagctgaag accatgcagg acagcgtgga      720
ggacttcaag actaagtatg aagaggagat caacaaacgc acagcagccg agaatgactt      780
tgtggtccta agaaggacg tggatgctgc ctacctgaac aaggtggagt tggaggccaa       840
ggtggacagt cttaatgacg agatcaactt cctgaaggtc ctctatgatg cggagctgtc      900
ccagatgcag acccatgtca gcgacacgtc cgtggtcctt ccatggaca acaaccgcaa       960 cctggacctg gacagcatta ttgccgaggt ccgtgcccag tacgaggaga ttgcccagag     1020
gagcaaggct gaggctgaag ccctgtacca gaccaaggtc cagcagctcc agatctcggt     1080
tgaccaacat ggtgacaacc tgaagaacac caagagtgaa attgcagagc tcaacaggat     1140
gatccagagg ctgcgggcag agatcgagaa catcaagaag cagtgccaga ctcttcaggt     1200
atccgtggct gatgcagagc agcgaggtga gaatgccctt aaagatgccc acagcaagcg     1260
cgtagagctg gaggctgccc tgcagcaggc caaggaggag ctggcacgaa tgctgcgtga     1320
gtaccaggag ctcatgagtg tgaagctggc cttggacatc gagatcgcca cctaccgcaa     1380
actgctggag ggcgaggagt acagaatgtc tggagaatgc agagtgccg tgagcatctc      1440 tgtggtcagc ggtagcacca gcactggagg catcagcgga ggattaggaa gtggctccgg     1500
gtttggcctg agtagtggct ttggctccgg ctctggaagt ggctttgggt tggtggcag       1560 tgtctctggc agttccagca gcaagatcat ctctaccacc ccctgaaca agagacgata      1620 gaggagacga ggtccctgca gctcactgtg tccagctggg cccagcactg gtgtctctgt     1680
gcttccttca cttcacctcc atcctctgtc tctggggctc atcttactag tatccctcc      1740 actatcccat gggctctctc tgccccagga tgatcttctg tgctgggaca gggactctgc     1800
ctcttggagt ttggtagcta cttcttgatt tgggcctggt gacccacctg gaatgggaag     1860
gatgtcagct gacctctcac ctcccatgga cagagaagaa aatgaccagg agtgtcatct     1920
ccagaattat tggggtcaca tatgtccctt cccagtccaa tgccatctcc cactagatcc     1980
tgtattatcc atctacatca gaaccaaact acttctccaa cacccggcag cacttggccc     2040
tgcaagctta ggatgagaac cacttagtgt cccattctac tcctctcatt ccctcttatc     2100
catctgcagg tgaatcttca ataaaatgct tttgtcattc attctga                   2147

<210> SEQ ID NO 4
<211> LENGTH: 2320
<212> TYPE: DNA
<213> ORGANISM: Homo sapiens

<400> SEQUENCE: 4
tcgacagctc tctcgcccag cccagttctg gaagggataa aaaggggca tcaccgttcc       60 tgggtaacag agccaccttc tgcgtcctgc tgagctctgt tctctccagc acctcccaac     120
ccactagtgc ctggttctct tgctccacca ggaacaagcc accatgtctc gccagtcaag     180
tgtgtccttc cggagcgggg gcagtcgtag cttcagcacc gcctctgcca tcaccccgtc     240
```

```
tgtctcccgc accagcttca cctccgtgtc ccggtccggg ggtggcggtg gtggtggctt    300
cggcagggtc agccttgcgg gtgcttgtgg agtgggtggc tatggcagcc ggagcctcta    360
caacctgggg ggctccaaga ggatatccat cagcactagt ggtggcagct tcaggaaccg    420
gtttggtgct ggtgctggag gcggctatgg ctttggaggt ggtgccggta gtggatttgg    480
tttcggcggt ggagctggtg gtggctttgg gctcggtggc ggagctggct ttggaggtgg    540
cttcggtggc cctggctttc ctgtctgccc tcctggaggt atccaagagg tcactgtcaa    600
ccagagtctc ctgactcccc tcaacctgca aatcgacccc agcatccaga gggtgaggac    660
cgaggagcgc gagcagatca agaccctcaa caataagttt gcctccttca tcgacaaggt    720
gcggttcctg gagcagcaga acaaggttct ggacaccaag tggaccctgc tgcaggagca    780
gggcaccaag actgtgaggc agaacctgga gccgttgttc gagcagtaca tcaacaacct    840
caggaggcag ctggacagca tcgtggggga acggggccgc ctggactcag agctgagaaa    900
catgcaggac ctggtggaag acttcaagaa caagtatgag gatgaaatca acaagcgtac    960
cactgctgag aatgagtttg tgatgctgaa gaaggatgta gatgctgcct acatgaacaa   1020
ggtggagctg gaggccaagg ttgatgcact gatggatgag attaacttca tgaagatgtt   1080
ctttgatgcg gagctgtccc agatgcagac gcatgtctct gacacctcag tggtcctctc   1140
catggacaac aaccgcaacc tggacctgga tagcatcatc gctgaggtca aggcccagta   1200
tgaggagatt gccaaccgca gccggacaga agccgagtcc tggtatcaga ccaagtatga   1260
ggagctgcag cagacagctg gccggcatgg cgatgacctc cgcaacacca agcatgagat   1320
ctctgagatg aaccggatga tccagaggct gagagccgag attgacaatg tcaagaaaca   1380
gtgcgccaat ctgcagaacg ccattgcgga tgccgagcag cgtggggagc tggccctcaa   1440
ggatgccagg aacaagctgg ccgagctgga ggaggccctg cagaaggcca gcaggacat    1500 ggcccggctg ctgcgtgagt accaggagct catgaacacc aagctggccc tggacgtgga   1560
gatcgccact taccgcaagc tgctggaggg cgaggaatgc agactcagtg agaaggagt    1620 tggaccagtc aacatctctg ttgtcacaag cagtgtttcc tctggatatg gcagtggcag   1680
tggctatggc ggtggcctcg gtggaggtct tggcggcggc ctcggtggag gtcttgccgg   1740
aggtagcagt ggaagctact actccagcag cagtgggggt gtcggcctag gtggtgggct   1800
cagtgtgggg ggctctggct tcagtgcaag cagtggccga gggctggggg tgggctttgg   1860
cagtggcggg ggtagcagct ccagcgtcaa atttgtctcc accacctcct cctcccggaa   1920
gagcttcaag agctaagaac ctgctgcaag tcactgcctt ccaagtgcag caacccagcc   1980
catggagatt gcctcttcta ggcagttgct caagccatgt tttatccttt tctggagagt   2040
agtctagacc aagccaattg cagaaccaca ttctttggtt cccaggagag ccccattccc   2100
agcccctggt ctcccgtgcc gcagttctat attctgcttc aaatcagcct tcaggtttcc   2160
cacagcatgg cccctgctga cacgagaacc caaagttttc ccaaatctaa atcatcaaaa   2220
cagaatcccc accccaatcc caaatttgt tttggttcta actacctcca gaatgtgttc   2280
aataaaatgc ttttataata taaaaaaaaa aaaaaaaaa                          2320
```

```
<210> SEQ ID NO 5
<211> LENGTH: 2450
<212> TYPE: DNA
<213> ORGANISM: Homo sapiens

<400> SEQUENCE: 5
```

```
atatttcata cctttctaga aactgggtgt gatctcactg ttggtaaagc ccagcccttc    60
ccaacctgca agctcacctt ccaggactgg gcccagccca tgctctccat atataagctg   120
ctgccccgag cctgattcct agtcctgctt ctcttccctc tctcctccag cctctcacac   180
tctcctcagc tctctcatct cctggaacca tggccagcac atccaccacc atcaggagcc   240
acagcagcag ccgccggggt ttcagtgcca actcagccag gctccctggg gtcagccgct   300
ctggcttcag cagcgtctcc gtgtcccgct ccagggcag tggtggcctg ggtggtgcat   360
gtggaggagc tggctttggc agccgcagtc tgtatggcct ggggggctcc aagaggatct   420
ccattggagg gggcagctgt gccatcagtg gcggctatgg cagcagagcc ggaggcagct   480
atggctttgg tggcgccggg agtggatttg gtttcggtgg tggagccggc attggctttg   540
gtctgggtgg tggagccggc cttgctggtg gctttggggg ccctggcttc cctgtgtgcc   600
cccctggagg catccaagag gtcaccgtca accagagtct cctgactccc ctcaacctgc   660
aaatcgatcc caccatccag cgggtgcggg ctgaggagcg tgaacagatc aagaccctca   720
acaacaagtt tgcctccttc atcgacaagg tgcggttcct ggagcagcag aacaaggttc   780
tggaaacaaa gtggaccctg ctgcaggagc agggcaccaa gactgtgagg cagaacctgg   840
agccgttgtt cgagcagtac atcaacaacc tcaggaggca gctggacagc attgtcgggg   900
aacggggccg cctggactca gagctcagag gcatgcagga cctggtggag gacttcaaga   960
acaaatatga ggatgaaatc aacaagcgca cagcagcaga gaatgaattt gtgactctga  1020
agaaggatgt ggatgctgcc tacatgaaca aggttgaact gcaagccaag gcagacactc  1080
tcacagacga gatcaacttc ctgagagcct tgtatgatgc agagctgtcc cagatgcaga  1140
cccacatctc agacacatct gtggtgctgt ccatggacaa caaccgcaac ctggacctgg  1200
acagcatcat cgctgaggtc aaggcccaat atgaggagat tgctcagaga agccgggctg  1260
aggctgagtc ctggtaccag accaagtacg aggagctgca ggtcacagca ggcagacatg  1320
gggacgacct cgcaacacc aagcaggaga ttgctgagat caaccgcatg atccagaggc  1380
tgagatctga gatcgaccac gtcaagaagc agtgcgccaa cctgcaggcc gccattgctg  1440
atgctgagca gcgtggggag atggcccctca aggatgccaa gaacaagctg aagggctgg  1500
aggatgccct gcagaaggcc aagcaggacc tggcccggct gctgaaggag taccaggagc  1560
tgatgaatgt caagctggcc ctggacgtgg agatcgccac ctaccgcaag ctgctggagg  1620
gtgaggagtg caggctgaat ggcgaaggcg ttggacaagt caacatctct gtggtgcagt  1680
ccaccgtctc cagtggctat ggcggtgcca gtggtgtcgg cagtggctta ggcctgggtg  1740
gaggaagcag ctactcctat ggcagtggtc ttggcgttgg aggtggcttc agttccagca  1800
gtggcagagc cattggggt ggcctcagct ctgttgagg cggcagttcc accatcaagt  1860
acaccaccac ctcctcctcc agcaggaaga gctataagca ctaaagtgcg tctgctagct  1920
ctcggtccca cagtcctcag gcccctctct ggctgcagag ccctctcctc aggttgcctt  1980
tcctctcctg gcctccagtc tcccctgctg tcccaggtag agctgggtat ggatgcttag  2040
tgccctcact tcttctctct ctctctatac catctgagca cccattgctc accatcagat  2100
caacctctga ttttacatca tgatgtaatc accactggag cttcactgtt actaaattat  2160
taatttcttg cctccagtgt tctatctctg aggctgagca ttataagaaa atgacctctg  2220
ctccttttca ttgcagaaaa ttgccagggg cttatttcag aacaacttcc acttactttc  2280
cactggctct caaactctct aacttataag tgttgtgaac ccccacccag gcagtatcca  2340
tgaaagcaca agtgactagt cctatgatgt acaaagcctg tatctctgtg atgatttctg  2400
```

-continued

| tgctcttcgc tgtttgcaat tgctaaataa agcagattta taatacaata | 2450 |

<210> SEQ ID NO 6
<211> LENGTH: 2331
<212> TYPE: DNA
<213> ORGANISM: Homo sapiens

<400> SEQUENCE: 6

| cgcctccagc ctctcacact ctcctaagcc ctctcatctc ctggaaccat ggccagcaca | 60 |
| tccaccacca tcaggagcca cagcagcagc cgccggggtt tcagtgccaa ctcagccagg | 120 |
| ctccctgggg tcagccgctc tggcttcagc agcatctccg tgtcccgctc caggggcagt | 180 |
| ggtggcctgg gtggcgcatg tggaggagct ggctttggca gccgcagtct gtatggcctg | 240 |
| gggggctcca agaggatctc cattggaggg gcagctgtg ccatcagtgg cggctatggc | 300 |
| agcagagccg gaggcagcta tggctttggt ggcgccggga gtggatttgg tttcggtggt | 360 |
| ggagccggca ttggctttgg tctggtggt ggagccggcc ttgctggtgg cttgggggc | 420 |
| cctggcttcc ctgtgtgccc cctggaggc atccaagagg tcactgtcaa ccagagtctc | 480 |
| ctgactcccc tcaacctgca aattgacccc gccatccagc gggtgcgggc cgaggagcgt | 540 |
| gagcagatca agaccctcaa caacaagttt gcctccttca tcgacaaggt gcggttccta | 600 |
| gagcagcaga caaggttct ggacaccaag tggaccctgc tgcaggagca gggcaccaag | 660 |
| actgtgaggc agaacctgga gccgttgttc gagcagtaca tcaacaacct caggaggcag | 720 |
| ctggacaaca tcgtggggga acggggtcgt ctggactcgg agctgagaaa catgcaggac | 780 |
| ctggtggagg acctcaagaa caaatatgag gatgaaatca acaagcgcac agcagcagag | 840 |
| aatgaatttg tgactctgaa gaaggatgtg gatgctgcct acatgaacaa ggttgaactg | 900 |
| caagccaagg cagacactct tacagatgag atcaacttcc tgagagcctt gtatgatgca | 960 |
| gagctgtccc agatgcagac ccacatctca gacacatccg tggtgctatc catggacaac | 1020 |
| aaccgcaacc tggacctgga cagcatcatc gctgaggtca aggcccaata tgaggagatt | 1080 |
| gctcagagga gcagggctga ggctgagtcc tggtaccaga caaagtacga ggagctgcag | 1140 |
| atcacagcag gcagacatgg ggacgacctg cgcaacacca gcaggagat tgctgagatc | 1200 |
| aaccgcatga tccagaggct gagatctgag atcgaccacg tcaagaagca gtgtgccaac | 1260 |
| ctacaggccg ccattgctga tgctgagcag cgtggggaga tggccctcaa ggatgctaag | 1320 |
| aacaagctgg aagggctgga ggatgccctg cagaaggcca gcaggacct ggcccggctg | 1380 |
| ctgaaggagt accaggagct gatgaacgtc aagctggccc tggatgtgga gatcgccacc | 1440 |
| taccgcaagc tgctggaggg cgaggagtgc aggctgaatg gcgaaggcgt tggacaagtc | 1500 |
| aacatctctg tagtgcagtc caccgtctcc agtggctatg gcggtgccag cggtgtcggc | 1560 |
| agtggcttag gcctgggtgg aggaagcagc tactcctatg gcagtggtct ggcgttgga | 1620 |
| ggcggcttta gttccagcag cggcagagcc actgggggtg gcctcagctc tgttggaggc | 1680 |
| ggcagttcca ccatcaagta caccaccacc tcctcctcca gcaggaagag ctacaagcac | 1740 |
| tgaagtgctg ccgccagctc tcagtcccac agctctcagg ccctctctg gcagcagagc | 1800 |
| cctctcctca ggttgcttgt cctccccctgg cctccagtct ccctgccct cccgggtaga | 1860 |
| gctgggatgc cctcactttt cttctcatca ataccgttc cactgagctc ctgttgctta | 1920 |
| ccatcaagtc aacagttatc agcactcaga catgcgaatg tccttttag ttcccgtatt | 1980 |
| attacaggta tctgagtctg ccataattct gagaagaaaa tgacctatat ccccataaga | 2040 |

```
actgaaactc agtctaggtc cagctgcaga tgaggagtcc tctctttaat tgctaaccat    2100
cctgcccatt atagctacac tcaggagttc tcatctgaca agtcagttgt cctgatcttc    2160
tcttgcagtg tccctgaatg gcaagtgatg taccttctga tgcagtctgc attcctgcac    2220
tgctttctct gctctctttg ccttcttttg ttctgttgaa taaagcatat tgagaatgtg    2280
aaaaaaaaaa aaaaaaaaaa aaaaaaaaaa aaaaaaaaaa aaaaaaaaaa a            2331

<210> SEQ ID NO 7
<211> LENGTH: 1753
<212> TYPE: DNA
<213> ORGANISM: Homo sapiens

<400> SEQUENCE: 7
cagccccgcc cctacctgtg aagcccagc cgcccgctcc cgcggataaa aggcgcggag      60
tgtccccgag gtcagcgagt gcgcgctcct cctcgcccgc cgctaggtcc atcccggccc    120
agccaccatg tccatccact tcagctcccc ggtattcacc tcgcgctcag ccgccttctc    180
gggccgcggc gcccaggtgc gcctgagctc cgctcgcccc ggcggccttg gcagcagcag    240
cctctacggc ctcggcgcct cacggccgcg cgtggccgtg cgctctgcct atggggggccc    300 ggtgggcgcc ggcatccgcg aggtcaccat taaccagagc ctgctggccc cgctgcggct    360
ggacgccgac ccctcccctcc agcgggtgcg ccaggaggag agcgagcaga tcaagaccct    420
caacaacaag tttgcctcct tcatcgacaa ggtgcggttt ctggagcagc agaacaagct    480
gctggagacc aagtggacgc tgctgcagga gcagaagtcg ccaagagca gccgcctccc    540 agacatcttt gaggcccaga ttgctggcct tcggggtcag cttgaggcac tgcaggtgga    600
tgggggccgc ctggaggcgg agctgcggag catgcaggat gtggtggagg acttcaagaa    660
taagtacgaa gatgaaatta accaccgcac agctgctgag aatgagtttg tggtgctgaa    720
gaaggatgtg gatgctgcct acatgagcaa ggtggagctg gaggccaagg tggatgccct    780
gaatgatgag atcaacttcc tcaggaccct caatgagacg gagttgacag agctgcagtc    840
ccagatctcc gacacatctg tggtgctgtc catggacaac agtcgctccc tggacctgga    900
cggcatcatc gctgaggtca aggcgcagta tgaggagatg gccaaatgca gccgggctga    960
ggctgaagcc tggtaccaga ccaagtttga ccctccag gcccaggctg ggaagcatgg    1020
ggacgacctc cggaataccc ggaatgagat ttcagagatg aaccgggcca tccagaggct    1080
gcaggctgag atcgacaaca tcaagaacca gcgtgccaag ttggaggccg ccattgccga    1140
ggctgaggag cgtggggagc tggcgctcaa ggatgctcgt gccaagcagg aggagctgga    1200
agccgccctg cagcggggca agcaggatat ggcacggcag ctgcgtgagt accaggaact    1260
catgagcgtg aagctggccc tggacatcga gatcgccacc taccgcaagc tgctggaggg    1320
cgaggagagc cggttggctg gagatggagt gggagccgtg aatatctctg tgatgaattc    1380
cactggtggc agtagcagtg gcggtggcat tgggctgacc ctcggggaa ccatgggcag    1440 caatgccctg agcttctcca gcagtgcggg tcctgggctc ctgaaggctt attccatccg    1500
gaccgcatcc gccagtcgca ggagtgcccg cgactgagcc gcctccacc actccactcc    1560 tccagccacc acccacaatc acaagaagat tcccacccct gcctccatg cctggtccca    1620 agacagtgag acagtctgga aagtgatgtc agaatagctt ccaataaagc agcctcattc    1680
tgaggcctga gtgatccacg tgaaaaaaaa aaaaaaaaaa aaaaaaaaaa aaaaaaaaaa    1740
aaaaaaaaaa aaa                                                       1753
```

<210> SEQ ID NO 8
<211> LENGTH: 1802
<212> TYPE: DNA
<213> ORGANISM: Homo sapiens

<400> SEQUENCE: 8

```
aaaaggccat tcctgagagc tctcctcacc aagaagcagc ttctccgctc cttctaggat      60
ctccgcctgg ttcggcccgc ctgcctccac tcctgcctct accatgtcca tcagggtgac     120
ccagaagtcc tacaaggtgt ccacctctgg cccccgggcc ttcagcagcc gctcctacac     180
gagtgggccc ggttcccgca tcagctcctc gagcttctcc cgagtgggca gcagcaactt     240
tcgcggtggc ctgggcggcg gctatggtgg ggccagcggc atgggaggca tcaccgcagt     300
tacggtcaac cagagcctgc tgagccccct tgtcctggag gtggacccca acatccaggc     360
cgtgcgcacc caggagaagg agcagatcaa gaccctcaac aacaagtttg cctccttcat     420
agacaaggta cggttcctgg agcagcagaa caagatgctg gagaccaagt ggagcctcct     480
gcagcagcag aagacggctc gaagcaacat ggacaacatg ttcgagagct acatcaacaa     540
ccttaggcgg cagctggaga ctctgggcca ggagaagctg aagctggagg cggagcttgg     600
caacatgcag gggctggtgg aggacttcaa gaacaagtat gaggatgaga tcaataagcg     660
tacagagatg gagaacgaat tgtcctcat caagaaggat gtggatgaag cttacatgaa     720
caaggtagag ctggagtctc gcctggaagg gctgaccgac gagatcaact tcctcaggca     780
gctatatgaa gaggagatcc gggagctgca gtcccagatc tcggacacat ctgtggtgct     840
gtccatggac aacagccgct ccctggacat ggacagcatc attgctgagg tcaaggcaca     900
gtacgaggat attgccaacc gcagccgggc tgaggctgag agcatgtacc agatcaagta     960
tgaggagctg cagagcctgg ctgggaagca cggggatgac ctgcggcgca caaagactga    1020
gatctctgag atgaaccgga acatcagccg gctccaggct gagattgagg gcctcaaagg    1080
ccagagggct tccctggagg ccgccattgc agatgccgag cagcgtggag agctggccat    1140
taaggatgcc aacgccaagt tgtccgagct ggaggccgcc ctgcagcggg ccaagcagga    1200
catggcgcgg cagctgcgtg agtaccagga gctgatgaac gtcaagctgg ccctggacat    1260
cgagatcgcc acctacagga agctgctgga gggcgaggag agccggctgg agtctggtat    1320
gcagaacatg agtattcata cgaagaccac cagcggctat gcaggtggtc tgagctcggc    1380
ctatgggggc ctcacaagcc ccggcctcag ctacagcctg ggctccagct ttggctctgg    1440
cgcgggctcc agctccttca gccgcaccag ctcctccagg gccgtggttg tgaagaagat    1500
cgagacacgt gatgggaagc tggtgtctga gtcctctgac gtcctgccca gtgaacagc    1560
tgcggcagcc cctcccagcc tacccctcct gcgctgcccc agagcctggg aaggaggccg    1620
ctatgcaggg tagcactggg aacaggagac ccacctgagg ctcagcccta gccctcagcc    1680
cacctgggga gtttactacc tggggacccc ccttgcccat gcctccagct acaaaacaat    1740
tcaattgctt tttttttttg gtccaaaata aacctcagc tagctctgcc aatgtcaaaa    1800
aa                                                                   1802
```

<210> SEQ ID NO 9
<211> LENGTH: 2162
<212> TYPE: DNA
<213> ORGANISM: Homo sapiens

<400> SEQUENCE: 9

```
cactccctgg gctaaacagc atcaccatgt ctgttcgata cagctcaagc aagcactact      60
```

```
cttcctcccg cagtggagga ggaggaggag gaggaggatg tggaggagga ggaggagtgt      120
catccctaag aatttctagc agcaaaggct cccttggtgg aggatttagc tcagggggt       180 tcagtggtgg ctcttttagc cgtgggagct ctggtggggg ctgctttggg ggctcatcag     240
gtggctatgg aggattagga ggttttggtg gaggtagctt tcgtggaagc tatggaagta     300
gcagctttgg tgggagttat ggaggcagct ttggaggggg cagtttcgga ggtggcagct     360
ttggtggggg cagctttggt ggaggcggct tggtggagg cggctttgga ggaggctttg      420
gtggtggatt tggaggagat ggtggccttc tctctggaaa tgaaaagta accatgcaga     480 atctgaatga ccgcctggct tcctacttgg acaaagttcg ggctctggaa gaatcaaact    540
atgagctgga aggcaaaatc aaggagtggt atgaaaagca tggcaactca catcagggg    600 agcctcgtga ctacagcaaa tactacaaaa ccatcgatga ccttaaaaat cagattctca    660
acctaacaac tgataatgcc aacatcctgc ttcagatcga caatgccagg ctggcagctg    720
atgacttcag gctgaagtat gagaatgagg tagctctgcg ccagagcgtg gaggctgaca    780
tcaacggcct gcgtagggtg ctggatgagc tgaccctgac caaggctgac ctggagatgc    840
aaattgagag cctgactgaa gagctggcct atctgaagaa gaaccacgag gaggaaatga    900
aagaccttcg aaatgtgtcc actggtgatg tgaatgtgga aatgaatgct gccccgggtg    960
ttgatctgac tcaacttctg aataacatga agccaata tgaacaactt gctgaacaaa      1020
accgcaaaga tgctgaagcc tggttcaatg aaaagagcaa ggaactgact acagaaattg    1080
ataataacat tgaacagata tccagctata atctgagat tactgaattg agacgtaatg     1140
tacaagctct ggagatagaa ctacagtccc aactggcctt gaaacaatcc ctggaagcct    1200
ccttggcaga aacagaaggt cgctactgtg tgcagctctc acagattcag gcccagatat    1260
ccgctctgga agaacagttg caacagattc gagctgaaac cgagtgccag aatactgaat    1320
accaacaact cctggatatt aagatccgac tggagaatga aattcaaacc taccgcagcc    1380
tgctagaagg agagggaagt tccggaggcg gcggacgcgg cggcggaagt ttcggcggcg    1440
gctacggcgg cggaagctcc ggcggcggaa gctccggcgg cggccacggc ggcggccacg    1500
gcggcagttc cggcggcggc tacgaggcg gaagctccgg cggcggaagc tccggcggcg    1560
gctacggggg cggaagctcc agcggcggcc acggcggcag ttccagcggc ggctacggtg    1620
gtggcagttc cggcggcggc ggcggcggct acggggcgg cagctccggc ggcggcagca    1680
gctccggcgg cggatacggc ggcggcagct ccagcggagg ccacaagtcc tcctcttccg    1740
ggtccgtggg cgagtcttca tctaagggac caagatacta caaaaccag agtaatcaag    1800 acaattattg aagaggtggc gcccgacggt agagttcttt catctatggt tgaatcagaa    1860
accaagaaac actactatta aactgcatca agaggaaaga gtctcccttc acacagacca    1920
ttatttacag atgcatggaa acaaagtct ccaagaaaac acttctgtct tgatggtcta     1980
tggaaataga ccttgaaaat aaggtgtcta caaggtgttt tgtggttcct gtatttcttc    2040
ttttcacttt accagaaagt gttctttaat ggaaagaaaa acaactttct gttctcattt    2100
actaatgaat ttcaataaac tttcttactg atgcaaacta aaaaaaaaaa aaaaaaaaa    2160 aa                                                                   2162
```

<210> SEQ ID NO 10
<211> LENGTH: 1719
<212> TYPE: DNA
<213> ORGANISM: Homo sapiens

<400> SEQUENCE: 10

```
cacagtcctc ggcccaggcc aagcaagctt ctatctgcac ctgctctcaa tcctgctctc    60
accatgagcc tccgcctgca gagctcctct gccagctatg gaggtggttt cggggggtggc   120 tcttgccagc tgggaggagg ccgtggtgtc tctacctgtt caactcggtt tgtgtctggg   180
ggatcagctg ggggctatgg aggcggcgtg agctgtggtt ttggtggagg ggctggtagt   240
ggctttggag gtggctatgg aggtggcctt ggaggtggct atggaggtgg ccttggaggt   300
ggctttggtg ggggttttgc tggtggcttt gttgactttg gtgcttgtga tggcggcctc   360
ctcactggca atgagaagat caccatgcag aacctcaacg accgcctggc ttcctacctg   420
gagaaggtgc gcgccctgga ggaggccaac gctgacctgg aggtgaagat ccgtgactgg   480
cacctgaagc agagcccagc tagccctgag cgggactaca gcccctacta caagaccatt   540
gaagagctcc gggacaagat cctgaccgcc accattgaaa caaccgggt catcctggag   600 attgacaatg ccaggctggc tgcggacgac ttcaggctca gtatgagaa tgagctggcc   660 ctgcgccaga gcgtggaggc cgacatcaac ggcctgcgcc gggtgctgga tgagctcact   720
ctgtctaaga ctgacctgga gatgcagatc gagagcctga tgaagagct agcctacatg   780 aagaagaacc atgaagagga gatgaaggaa tttagcaacc aggtggtcgg ccaggtcaac   840
gtggagatgg atgccacccc aggcattgac ctgacccgcg tgctggcaga gatgagggag   900
cagtacgagg ccatggcaga gaggaaccgc cgggatgctg aggaatggtt ccacgccaag   960
agtgcagagc tgaacaagga ggtgtctacc aacactgcca tgattcagac cagcaagaca  1020
gagatcacgg agctcaggcg cacgctccaa ggcctggaga ttgagctgca gtcccagctg  1080
agcatgaaag cggggctgga gaacacggtg gcagagacgg agtgccgcta tgccctgcag  1140
ctgcagcaga tccagggact catcagcagc atcgaggccc agctgagcga gctccgcagt  1200
gagatggagt gccagaacca agagtacaag atgctgctgg acatcaagac acgtctggag  1260
caggagatcg ccacctaccg cagcctgctc gagggccagg acgccaagat gattggtttc  1320
ccttcctcag caggaagcgt cagcccccgt agcacctctg ttaccacgac ttctagtgcc  1380
tctgttacca ccacctctaa tgcctctggt cgccgcactt ctgatgtccg taggccttaa  1440
atctgcctgg cgtcccctcc ctctgtcttc agcacccaga ggaggagaga gccggcagtt  1500
ccctgcagga gagaggaggg gctgctggac ccaaggctca gtccctctgc tctcaggacc  1560
ccctgtcctg actctctcct gatggtgggc cctctgtgct cttctcttcc ggtcggatct  1620
ctctcctctc tgacctggat acgctttggt ttctcaactt ctctacccca aagaaaagat  1680
tattcaataa agtttcctgc ctttctgcaa acataaaaa                          1719
```

<210> SEQ ID NO 11  
<211> LENGTH: 1693  
<212> TYPE: DNA  
<213> ORGANISM: Homo sapiens

<400> SEQUENCE: 11

```
cacagtcctc ggcccaggcc aagcaagctt ctatctgcac ctgctctcaa tcctgctctc    60
accatgagcc tccgcctgca gagctcctct gccagctatg gaggtggttt cggggggtggc   120 tcttgccagc tgggaggagg ccgtggtgtc tctacctgtt caactcggtt tgtgtctggg   180
ggatcagctg ggggctatgg aggcggcgtg agctgtggtt ttggtggagg ggctggtagt   240
ggctttggag gtggctatgg aggtggcctt ggaggtggct atggaggtgg ccttggaggt   300
ggctttggtg ggggttttgc tggtggcttt gttgactttg gtgcttgtga tggcggcctc   360
```

```
ctcactggca atgagaagat caccatgcag aacctcaacg accgcctggc ttcctacctg      420
gagaaggtgc gcgccctgga ggaggccaac gctgacctgg aggtgaagat ccgtgactgg      480
cacctgaagc agagcccagc tagccctgag cgggactaca gccectacta caagaccatt      540 gaagagctcc gggacaagat cctgaccgcc accattgaaa caaccgggt catcctggag       600 attgacaatg ccaggctggc tgcggacgac ttcaggctca gtatgagaa tgagctggcc       660 ctgcgccaga gcgtggaggc cgacatcaac ggcctgcgcc gggtgctgga tgagctcact      720
ctgtctaaga ctgacctgga gatgcagatc gagagcctga tgaagagct agcctacatg       780 aagaagaacc atgaagagga gatgaaggaa tttagcaacc aggtggtcgg ccaggtcaac      840
gtggagatgg atgccacccc aggcattgac ctgacccgcg tgctggcaga gatgagggag      900
cagtacgagg ccatggcaga gaggaaccgc cgggatgctg aggaatggtt ccacgccaag      960
agtgcagagc tgaacaagga ggtgtctacc aacactgcca tgattcagac cagcaagaca     1020
gagatcacgg agctcaggcg cacgctccaa ggcctggaga ttgagctgca gtcccagctg     1080
agcatgaaag cggggctgga gaacacggtg gcagagacga gtgccgcta tgccctgcag      1140 ctgcagcaga tccagggact catcagcagc atcgaggccc agctgagcga gctccgcagt     1200
gagatggagt gccagaacca agagtacaag atgctgctgg acatcaagac acgtctggag     1260
caggagatcg ccacctaccg cagcctgctc gagggccagg acgccaagaa gcgtcagccc     1320
ccgtagcacc tctgttacca cgacttctag tgcctctgtt accaccacct ctaatgcctc     1380
tggtcgccgc acttctgatg tccgtaggcc ttaaatctgc ctggcgtccc ctccctctgt     1440
cttcagcacc cagaggagga gagagccggc agttccctgc aggagagagg aggggctgct     1500
ggacccaagg ctcagtccct ctgctctcag gaccccctgt cctgactctc tcctgatggt     1560
gggccctctg tgctcttctc ttccggtcgg atctctctcc tctctgacct ggatacgctt     1620
tggtttctca acttctctac cccaaagaaa agattattca ataaagtttc ctgcctttct     1680
gcaaacataa aaa                                                        1693

<210> SEQ ID NO 12
<211> LENGTH: 1485
<212> TYPE: DNA
<213> ORGANISM: Homo sapiens

<400> SEQUENCE: 12
tccggggcgg gggcggggcc tcactctgcg atataactcg ggtcgcgcgg ctcgcgcagg       60
ccgccaccgt cgtccgcaaa gcctgagtcc tgtcctttct ctctccccgg acagcatgag      120
cttcaccact cgctccacct tctccaccaa ctaccggtcc ctgggctctg tccaggcgcc      180
cagctacggc gcccggccgg tcagcagcgc ggccagcgtc tatgcaggcg ctgggggctc      240
tggttcccgg atctccgtgt cccgctccac cagcttcagg ggcggcatgg ggtccggggg      300 cctgccacc gggatagccg ggggtctggc aggaatggga ggcatccaga acgagaagga       360
gaccatgcaa agcctgaacg accgcctggc ctcttacctg gacagagtga ggagcctgga      420
gaccgagaac cggaggctgg agagcaaaat ccggagcac ttggagaaga agggaccccca      480 ggtcagagac tggagccatt acttcaagat catcgaggac ctgagggctc agatcttcgc      540
aaatactgtg gacaatgccc gcatcgttct gcagattgac aatgcccgtc ttgctgctga      600
tgactttaga gtcaagtatg agacagagct ggccatgcgc cagtctgtgg agaacgacat      660
ccatgggctc cgcaaggtca ttgatgacac caatatcaca cgactgcagc tggagacaga      720
```

```
gatcgaggct ctcaaggagg agctgctctt catgaagaag aaccacgaag aggaagtaaa      780
aggcctacaa gcccagattg ccagctctgg gttgaccgtg gaggtagatg cccccaaatc      840
tcaggacctc gccaagatca tggcagacat ccgggcccaa tatgacgagc tggctcggaa      900
gaaccgagag gagctagaca agtactggtc tcagcagatt gaggagagca ccacagtggt      960
caccacacag tctgctgagg ttggagctgc tgagacgacg ctcacagagc tgagacgtac     1020
agtccagtcc ttggagatcg acctggactc catgagaaat ctgaaggcca gcttggagaa     1080
cagcctgagg gaggtggagg cccgctacgc cctacagatg gagcagctca acgggatcct     1140
gctgcacctt gagtcagagc tggcacagac ccgggcagag ggacagcgcc aggcccagga     1200
gtatgaggcc ctgctgaaca tcaaggtcaa gctggaggct gagatcgcca cctaccgccg     1260
cctgctggaa gatggcgagg actttaatct tggtgatgcc ttggacagca gcaactccat     1320
gcaaaccatc caaaagacca ccacccgccg gatagtggat ggcaaagtgg tgtctgagac     1380
caatgacacc aaagttctga ggcattaagc cagcagaagc agggtaccct ttggggagca     1440
ggaggccaat aaaaagttca gagttcaaaa aaaaaaaaaa aaaaa                     1485
```

<210> SEQ ID NO 13
<211> LENGTH: 1439
<212> TYPE: DNA
<213> ORGANISM: Homo sapiens

<400> SEQUENCE: 13

```
gcagcctcga gggccaacaa cacctgctgt ccgtgtccat gccggttgg ccaccccgtt       60 tctgggggca tgagcttcac cactcgctcc accttctcca ccaactaccg gtccctgggc     120
tctgtccagg cgcccagcta cggcgcccgg ccggtcagca gcgcggccag cgtctatgca     180
ggcgctgggg gctctggttc ccggatctcc gtgtcccgct ccaccagctt caggggcggc     240
atggggtccg ggggcctggc caccgggata gccggggtc tggcaggaat gggaggcatc      300
cagaacgaga aggagaccat gcaaagcctg aacgaccgcc tggcctctta cctggacaga     360
gtgaggagcc tggagaccga gaccggagg ctggagagca aaatccggga gcacttggag      420
aagaagggac cccaggtcag agactggagc cattacttca agatcatcga ggacctgagg     480
gctcagatct tcgcaaatac tgtggacaat gcccgcatcg ttctgcagat tgacaatgcc     540
cgtcttgctg ctgatgactt tagagtcaag tatgagacag agctggccat gcgccagtct     600
gtggagaacg acatccatgg gctccgcaag gtcattgatg acaccaatat cacacgactg     660
cagctggaga cagagatcga ggctctcaag gaggagctgc tcttcatgaa gaagaaccac     720
gaagaggaag taaaaggcct acaagcccag attgccagct ctgggttgac cgtggaggta     780
gatgccccca atctcaggga cctgccaag atcatggcag acatccgggc caatatgac      840 gagctggctc ggaagaaccg agaggagcta gacaagtact ggtctcagca gattgaggag     900
agcaccacag tggtcaccac acagtctgct gaggttggag ctgctgagac gacgctcaca     960
gagctgagac gtacagtcca gtccttggag atcgacctgg actccatgag aaatctgaag    1020
gccagcttgg agaacagcct gagggaggtg gaggcccgct acgccctaca gatggagcag    1080
ctcaacggga tcctgctgca ccttgagtca gagctggcac agacccgggc agagggacag    1140
cgccaggccc aggagtatga ggccctgctg aacatcaagg tcaagctgga ggctgagatc    1200
gccacctacc gccgcctgct ggaagatggc gaggacttta atcttggtga tgccttggac    1260
```

```
agcagcaact ccatgcaaac catccaaaag accaccaccc gccggatagt ggatggcaaa    1320
gtggtgtctg agaccaatga caccaaagtt ctgaggcatt aagccagcag aagcagggta    1380 cccttt gggg agcaggaggc caataaaaag ttcagagttc aaaaaaaaaa aaaaaaaa     1439
```

ENRICHMENT AND IDENTIFICATION OF FETAL CELLS IN MATERNAL BLOOD AND LIGANDS FOR SUCH USE

BACKGROUND

The examination of fetal cells for early detection of fetal diseases and genetic abnormalities is carried out in connection with many pregnancies, in particular when the maternal age is high (35 years or above) or where genetic diseases are known in the family. Fetal cells may be obtained by amniocentesis, the removal of amniotic fluid from the amniotic cavity within the amniotic sac or by chorion biopsy, where biopsies are taken from the placenta, so-called invasive sampling.

Prenatal aneuploidy screening employs either traditional chromosome analysis or chromosome specific DNA probes for elucidation of numerical aberrations of the most frequently abnormal chromosomes, particular chromosomes 13, 18, 21, X and Y in the fetus.

Due to the invasiveness of the sampling methods described above and the risk of abortion, it would be advantageously to perform fetal diagnosis by a non-invasive procedure, such as for example by use of a maternal blood sample.

During pregnancy a variety of cell types of fetal origin cross the placenta and circulate within maternal peripheral blood. The feasibility of using fetal cells in the maternal circulation for diagnostic purposes has been hindered by the fact that fetal cells are present in maternal blood in only very limited numbers, reported numbers have been from one fetal cell per $10^5$-$10^8$ nucleated maternal cells or 1-10 fetal cells per ml maternal blood. In addition most fetal cells cannot be distinguished from maternal cells on the basis of morphology alone, thus alternative methods of identification of fetal cells have been investigated.

US2007/0015171 describes a non-invasive method for isolation and detection of fetal DNA. The method enriches a maternal blood sample using antibodies that bind specifically to maternal cells and/or antibodies that bind specifically to fetal cells. The inventors suggest the use of a few specifically mentioned antibodies: HLe-1 is an antibody that recognizes an antigen present on mature human leucocytes and on very immature erythrocytes precursors, but not mature nucleated erythrocytes. Thus, it is suggested that this antibody can be used to recognize maternal leucocytes, but not fetal nucleated erythrocytes. Anti-monocyte antibody (M3) and anti-lymphocyte antibody (L4) are also suggested for removing maternal cells from a sample. Finally, the authors suggest using a monoclonal antibody, which recognizes the transferrin receptor (TfR) on fetal cells. DNA from isolated fetal cells is subsequently made available for detection and diagnosis.

WO2008/132753 describes a method of identifying a trophoblast by detecting in cells of a biological sample expression of a trophoblast marker selected from the group consisting of an annexin IV, a cytokeratin-7, a cytokeratin 8 and a cytokeratin-19. A trophoblast is referred to as an epithelial cell which is derived from the placenta of a mammalian embryo or fetus; a trophopblast typically contacts the uterine wall. Three types of trophoblasts are mentioned, the villous cytotrophoblast, the syncytiotrophoblast and the extravillous trophoblast. Importantly, the inventors used monoclonal antibodies against Vimentin to estimate the extent of fibroblast contamination of trophoblasts isolated from first trimester placentas. Thus, the trophoblasts isolated by these inventors do not comprise Vimentin.

Gussin et al., 2004, hypothesized that fetal cells in maternal blood that do not respond to hematopoietic culture conditions represent endothelial cells. They investigated whether endothelial progenitor cells of fetal origin may be selected from maternal blood on the basis of their expression of CD133 or CD105 and expanded in culture. The authors concluded that CD133+ and CD105+ cells isolated from maternal blood can be expanded in vitro under endothelial conditions. These cells appear to be of maternal, rather than fetal, origin.

Thus, there remains a need for improved methods of isolating fetal cells from maternal blood samples such as to facilitate pre-natal detection and diagnosis.

SUMMARY OF THE INVENTION

The present invention is based on the identification of antigens that can be used for identification and/or enrichment of fetal cells of a maternal blood sample. In particular the invention is based on the surprising finding that fetal cells in a maternal blood sample displays both endothelial and epithelial characteristics. By utilizing this transition the inventors provides a new method for enriching and identifying fetal cells in a maternal blood sample and also discloses new antigens for this purpose.

In a preferred first embodiment of the invention the maternal blood sample is contacted with an endothelial cell marker and the cells with endothelial phenotype is thereby enriched by selecting the cells specific for said endothelial cell marker. Such a method of identifying a fetal cell in a maternal blood sample comprises the steps of:

a. Providing a maternal blood sample or a fraction thereof
b. Contacting the sample with a hybridization probe comprising at least 10 contiguous nucleotides complementary to a gene encoding an endothelial cell marker or a ligand binding to an endothelial cell marker and
c. enriching the cells specific for said endothelial cell marker.
d. Contacting the cells selected in b) demonstrating an endothelial phenotype with a hybridization probe comprising at least 10 contiguous nucleotides complementary to a gene encoding an epithelial cell marker or a ligand directed to an epithelial cell marker
e. Detecting the cells with endothelial phenotype also binding the epithelial cell marker of step c).
f. Optionally, diagnosing and/or predicting the genetic content of the cells detected in d)

wherein step b-e may be performed in any order

DISCLOSURE OF THE INVENTION

Figure 1:
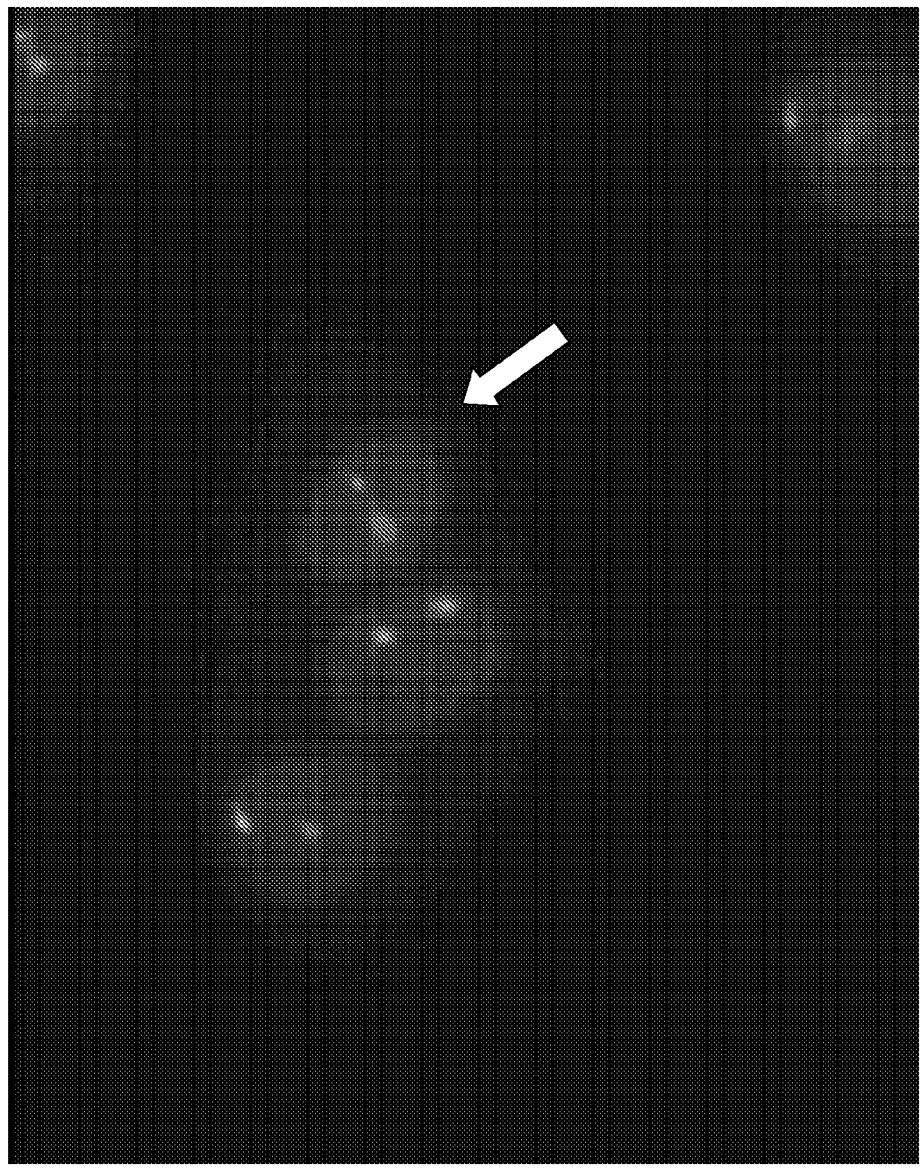
FIG. 1. Male fetal cell identified by X and Y specific probes. The arrow indicates the fetal cell.

The present invention is based on the identification of antigens that can be used for identification and/or enrichment of fetal cells of a maternal blood sample. In particular the invention is based on the surprising finding that fetal cells in a maternal blood sample displays both endothelial and epithelial characteristics. The present invention for the first time discloses that fetal cells present in a maternal blood sample undergoes a unique transition which none of the normal maternal cells in blood do. Already from the early blastocyst stadium the cells of the embryo differentiates into three germ layers, namely endoderm, mesoderm and ectoderm. Mesoderm represents soft tissue cells such as muscles, fat and blood vessels. Ectoderm and endoderm represents epithelial cells covering the outer and inner surfaces. Mesodermal and ectodermal cells have distinct differences in marker expression pattern.

Epithelial-mesenchymal transition (EMT) is a process by which epithelial cells lose their epithelial characteristics and acquire a mesenchymal-like phenotype. EMT has been described in early embryogenesis where migration and transient dedifferentiation of embryonic epithelial cells are required for the formation of e.g. the neural tube.

EMT has also been described in relation to cancer where several oncogenic pathways induce EMT. EMT has especially been studied in relation to the metastatic process in the recent years.

The present invention relates to the realization made by the inventors that fetal cells present in the maternal blood undergoes EMT and by utilizing this characteristic the present invention provides a new method of isolating and identifying fetal cells present in a maternal blood sample. By utilizing a mesoderm marker (i.e. an endothelial marker) as a positive selection marker the fetal cells present in a very low number in a maternal blood sample is enriched together with some maternal cells. Positive identification of the fetal cells is subsequently done by contacting the remaining cells with an epithelial marker thereby utilizing the EMT phenomenon. None of the normal maternal cells present in a blood sample is expressing any epithelial markers.

By utilizing this transition the inventors provides a new method for enriching and identifying fetal cells in a maternal blood sample and also discloses new antigens for this purpose.

Thus the methods of the invention comprise isolation of cells expressing endothelial cell markers followed by detection of cells, which in addition expresses epithelial cell markers.

The identified antigens may be used for identification of fetal cells in a maternal blood sample by detecting or quantifying the mRNA or the protein (antigen) encoded by the mRNA. When the term detection is used herein, it covers both detection and quantification. In two separate embodiments however, the term detection covers either detection or quantification. Generally, the skilled man will recognize when detection also covers quantification, i.e. when it is relevant to quantify mRNA levels or the levels of the protein encoded by the mRNAs. This may e.g. be necessary for detection of a given mRNA which is expressed at a low level in maternal cells (but not absent) and where the same mRNA is expressed at e.g. 3 fold higher levels in fetal cells.

When the term enriching is used herein, it covers isolation of one or more cell(s) from any of the other cells present in the sample. In one embodiment the enriched cell(s) is not isolated from the sample but rather any diagnosing is performed on the cell(s) while still present in the sample. The sample may then be present on a glass slide and the diagnosis may be performed using microscopy and the cells are in this embodiment rather detected than isolated.

Another discovery that the present inventors have made is that a step of fixing the cells of the maternal sample greatly aids identification and enrichment of fetal cells from the sample. This fixation step may be performed together with the methods of enriching and/or identifying fetal cells described herein or together with methods of enriching and/or identifying fetal cells that have been described in the prior art (e.g. US2007/0015171 described in the background section).

Fixation of the Cells of a Maternal Blood Sample

In one embodiment of the invention the discovery that fixation of the cells of a maternal blood sample greatly increases stability of fetal cells in a maternal blood sample, while allowing enrichment and identification of fetal cells e.g. as further described herein above. In one embodiment the fixation procedure can be performed on a non-enriched blood sample immediately after sampling (i.e. step a of the method described in the first embodiment), resulting in fixation of cellular components in the maternal blood sample. At the same time the fixation is so mild that maternal erythrocytes can be lysed selectively in a subsequent lysis step. The fixation may in one embodiment be performed at any suitable time point between step a-d of the method described in the first embodiment. In one embodiment fixation is performed after step a of the method described in the first embodiment. In another embodiment the fixation is performed after step b of the method described in the first embodiment. In another embodiment the fixation is performed after step c of the method described in the first embodiment. In yet another embodiment the fixation is performed after step d of the method described in the first embodiment.

In a preferred embodiment the method of the first embodiment of the invention as described in the "Summary of Invention" comprises the following steps:
   a. Providing a maternal blood sample or a fraction thereof
   b. Fixating the cells of said maternal blood sample,
   c. Contacting the sample with a hybridization probe comprising at least 10 contiguous nucleotides complementary to a gene encoding an endothelial cell marker or a ligand binding to an endothelial cell marker and
   d. enriching the cells specific for said endothelial cell marker.
   e. Contacting the cells selected in b) demonstrating an endothelial phenotype with a hybridization probe comprising at least 10 contiguous nucleotides complementary to a gene encoding an epithelial cell marker or a ligand directed to an epithelial cell marker
   f. Detecting the cells with endothelial phenotype also binding the epithelial cell marker of step c).
   g. Optionally, diagnosing and/or predicting the genetic content of the cells detected in d)
wherein the steps c-e may be performed in any order.

Thus, one embodiment of the invention is a method comprising the steps
   a. Providing a maternal blood sample or a fraction thereof
   b. Contacting the sample with a fixation solution Preferably, the maternal blood sample is contacted with the fixation solution immediately after the sample has been obtained. The term immediately as used in the present context means that the sample is not subjected to any other manipulations before being contacted with the fixation solution. Preferably, the sample is contacted with the fixation solution no more than 24 hours after the sample has been provided. More preferably, the sample is contacted with the fixation solution no more than 12 hours, such as 8 hours, 4 hours, 2 hours, 1 hour, 30 minutes, 15 minutes after the sample has been provided. Most preferably, the sample is contacted with the fixation solution no more than 1 hour after the sample has been provided.

In another preferred embodiment, the fixation solution is added to whole blood and preferably before an optional sedimentation step such as e.g. sedimentation by gravity or sedimentation by centrifugation.

Fixation is preferably done for between 1 and 60 minutes. More preferably, fixation is done for between 5 and 30 min and most preferably, fixation is done between 5 and 15 minutes such as 10 minutes.

The fixation solution preferably comprises between 2.5% and 7.5% paraformaldehyde, more preferably between 3% and 6%, and most preferably between 4% and 5%.

In addition to paraformaldehyde, the fixation solution preferably comprises salt at a concentration between 0.05 M and 0.3 M. More preferably the concentration is between 0.1 and 0.2 M and most preferred is a concentration between 0.125 and 0.175 M. The salt is preferably LiCl, KCl, NaCl or PBS, with PBS being most preferred.

When the above mentioned concentrations of the fixation solution are used, it is preferred to add between 0.2 and 10 volumes of the fixation solution to the maternal blood sample for fixation, more preferably between 0.5 and 5 volumes is added and most preferably between 1 and 3 volumes is added. Typically ⅔ volumes are added. In yet another embodiment, it is preferred to add between ⅓ and 3/3 volume of fixation solution, e.g. ⅔ volume.

It will be clear to the skilled man that the various concentrations of the fixation solution and folds of dilution can be adjusted such as to give the desired final concentrations after the fixation solution has been added to maternal blood sample. Preferably, the final concentration of paraformaldehyde is between 2 and 6%, more preferably between 3 and 5% and most preferably between 3.5% and 4.5%. A typical final concentration is 4%.

Preferably, the fixation step is followed by a step of lysis comprising:
  c. Contacting the fixed sample of step a with a lysis buffer The lysis buffer typically comprises a non-ionic detergent, preferably Triton X-100. Preferred concentrations of the detergent are between 0.01% (w/w) and 0.5%, more preferably between 0.05%-0.3%, and most preferably 0.1%.

In a preferred embodiment, the lysis step is performed immediately after the fixation step. That is both the fixation and the lysis is performed after step a and before step b of the method described in the first embodiment. I.e. the lysis solution is added directly to the sample, e.g. after fixation for 10 minutes. Lysis is typically done for a period of 15 minutes to 120 minutes, more preferably 30 to 60 minutes and most preferably for 40 to 45 minutes.

As mentioned above, the lysis step surprisingly allows selective lysis of maternal erythrocytes.

Another embodiment of the invention is the use of the lysis buffer for selective lysis of maternal erythrocytes in a maternal blood sample or a fraction thereof, as described herein above. In a preferred embodiment, the lysis buffer is for use in the method of the present invention and the lysis buffer may be added to the maternal blood sample or a fraction thereof after step a of the method described in the first embodiment.

Contacting the Maternal Blood Sample with a Ligand or a Probe

One embodiment of the present invention provides a method of selecting a fetal cell in a maternal blood sample, said method comprising the steps of a. Providing a maternal blood sample or a fraction thereof
  b. Contacting the sample with
    i. a hybridization probe comprising at least 10 contiguous nucleotides complementary to a gene encoding an endothelial cell marker or
    ii. a ligand directed to an endothelial cell marker
  c. Selecting cells that bind the hybridization probe or the ligand of the previous step and thereby enriching the sample for cells that bind the hybridization probe or the ligand of the previous step
  d. Contacting the (enriched) sample of step with
    i. a hybridization probe comprising at least 10 contiguous nucleotides complementary to a gene encoding an epithelial cell marker or
    ii. a ligand directed to an epithelial cell marker.

Preferably, the method further comprises a step of identifying fetal cells of the sample. As will be clear, identification preferably comprises detecting the presence of the ligand directed to an epithelial cell marker on or in the fetal cell or detecting the presence of an a hybridization probe comprising at least 10 contiguous nucleotides complementary to a gene encoding an epithelial cell marker on or in the fetal cell.

In a preferred embodiment the maternal blood sample is contacted with ligand or hybridization probe binding an endothelial cell marker or a gene encoding said marker and the cells with endothelial phenotype is thereby enriched by selecting the cells specific for said endothelial cell marker. Such a method comprises the steps of:
  a. Providing a maternal blood sample or a fraction thereof
  b. Contacting the sample with a hybridization probe comprising at least 10 contiguous nucleotides complementary to a gene encoding an endothelial cell marker or a ligand directed to an endothelial cell marker and
  c. selecting the cells specific for said endothelial cell marker thereby enriching the sample for cells with endothelial phenotype
  d. Contacting the cells selected in c) demonstrating an endothelial phenotype with a hybridization probe comprising at least 10 contiguous nucleotides complementary to a gene encoding an epithelial cell marker or a ligand directed to an epithelial cell marker
  e. Detecting the cells with endothelial phenotype also binding the epithelial cell marker of step d).
  f. Optionally, diagnosing and/or predicting the genetic content of the cells detected in e)
wherein step b-e may be performed in any order.

The skilled person would know that in one embodiment steps b, c, d, e and f described above may be performed in any order, preferably in the order described above or in the order b, d, c, e and f, more preferably in the order described above. Thus, in one embodiment the sample is contacted with a hybridization probe or ligand directed to an endothelial cell marker followed by contacting the same sample with a hybridization probe or ligand directed to an epithelial cell marker before the selection step is performed.

In a preferred embodiment, the endothelial cell marker is selected from the group consisting of CD105, CD146 or CD141, Vimentin, VCAM, ICAM, VEGFR-1, VEGFR-2, VEGFR-3, ITGA5, ITGB5, CDH11 or CDH3. An endothelial marker of the present invention is a marker which is expressed primarily in or on endothelial cells. Said endothelial marker is not particularly expressed in or on any other cell type. Most preferred is CD105 (SEQ ID NO 1 and SEQ ID NO 2).

In a preferred embodiment, the epithelial cell marker is selected from the group consisting of CK1, CK2, CK3, CK4, CK5, CK6, CK7, CK8, CK9, CK10, CK10, CK13, CK14, CK15, CK16, CK17, CK18 or CK19. An epithelial marker of the present invention is a marker which is expressed primarily in or on epithelial cells. Said epithelial marker is not particularly expressed in or on any other cell type.

In a preferred embodiment, the method further comprises contacting the sample with M30 antibody (or another ligand directed to apoptotic CK18). In a preferred embodiment the epithelial marker is selected from the group consisting of: CK4, CK5, CK6A, CK6B, CK7, CK8, CK10, CK13 and CK18. Most preferred id CK18 (SEQ ID NO: 12 and SEQ ID NO 13).

The antigens for use in the present invention and encoding genes are identified in table 1.

TABLE 1

| NCBI accession: | Short | Accession nr. |
|---|---|---|
| Human Endoglin | CD 105 | AF035753 |
| Human Vimentin | Vim | NM_003380 |
| Human Cytokeratin 1 | KRT1 | X69725 |
| Human Cytokeratin 2 | KRT2 | NM_000423 |
| Human Cytokeratin 3 | KRT3 | NM_057088 |
| Human Cytokeratin 4 | KRT4 | NM_002272 |
| Human Cytokeratin 5 | KRT5 | NM_000424 |
| Human Cytokeratin 6 | KRT6 | NM_080747 |
| Human Cytokeratin 7 | KRT7 | NM_005556 |
| Human Cytokeratin 8 | KRT8 | NM_002273 |
| Human Cytokeratin 10 | KRT10 | NM_000421 |
| Human Cytokeratin 13 | KRT13 | NM_153490 |
| Human Cytokeratin 14 | KRT14 | NM_000526 |
| Human Cytokeratin 15 | KRT15 | NM_002275 |
| Human Cytokeratin 16 | KRT16 | NM_005557 |
| Human Cytokeratin 17 | KRT17 | NM_000422 |
| Human Cytokeratin 18 | KRT18 | NM_199187 |
| Human Cytokeratin 19 | KRT19 | NM_002276 |
| Vascular Cell Adhesion Molecule | VCAM | P19320 |
| Intercellular Adhesion Molecule 1 | ICAM | NP_000192 |
| CD9 Molecule | CD9 | NP_001760 |
| Vascular Endothelial Growth Factor Receptor 1 (Flt-1) | VEGFR-1 | P17948 |
| Vascular Endothelial Growth Factor Receptor 2 | VEGFR-2 | P35968 |
| Vascular Endothelial Growth Factor Receptor 3 | VEGFR-3 | P35916 |
| Integrin, alpha V | ITGA5 | AAI36443 |
| Integrin, beta V | ITGB5 | ABY87537 |
| Cadherin 11 | CDH11 | EAW83002 |
| Cadherin 3 | CDH3 | P22223 |
| Carboxypeptidase M | CPM | AAH22276 |
| Lymphoid Cell Activation Antigen | CD39 | AAB32152 |
| Plasminogen Activator Inhibitor 1 | PAI-1 | P05121 |
| CD200 Molecule | CD200 | AAH31103 |
| EPH Receptor B4 | EPHB4 | EAL23820 |
| Endothelial Protein C Receptor | EPCR | AAH14451 |
| Proteinase Activated Receptor 1 | PAR-1 | P25116 |

The antigens for use in step b of the method described in the first embodiment and encoding genes are preferably selected from table 2. Thus, the endothelial cell marker of step b) of the method of the first embodiment of the invention described in the Summary of the invention is preferably selected from the markers encoded by the genes of table 2:

TABLE 2

| NCBI accession: | Short | Accession nr. |
|---|---|---|
| Human Endoglin | CD 105 | AF035753 |
| Human Vimentin | Vim | NM_003380 |
| Vascular Cell Adhesion Molecule | VCAM | P19320 |
| Intercellular Adhesion Molecule 1 | ICAM | NP_000192 |

TABLE 2-continued

| NCBI accession: | Short | Accession nr. |
|---|---|---|
| Vascular Endothelial Growth Factor Receptor 1 (Flt-1) | VEGFR-1 | P17948 |
| Vascular Endothelial Growth Factor Receptor 2 | VEGFR-2 | P35968 |
| Vascular Endothelial Growth Factor Receptor 3 | VEGFR-3 | P35916 |
| Plasminogen Activator Inhibitor 1 | PAI-1 | P05121 |
| Endothelial Protein C Receptor | EPCR | AAH14451 |

The antigens for use in step d of the method described in the first embodiment and encoding genes are preferably selected from table 3. Thus, the epithelial cell marker of step d) of the method of the first embodiment of the invention described in the Summary of the invention is preferably selected from the markers encoded by the genes of table 3:

TABLE 3

| NCBI accession: | Short | Accession nr. |
|---|---|---|
| Human Cytokeratin 1 | KRT1 | X69725 |
| Human Cytokeratin 2 | KRT2 | NM_000423 |
| Human Cytokeratin 3 | KRT3 | NM_057088 |
| Human Cytokeratin 4 | KRT4 | NM_002272 |
| Human Cytokeratin 5 | KRT5 | NM_000424 |
| Human Cytokeratin 6 | KRT6 | NM_080747 |
| Human Cytokeratin 7 | KRT7 | NM_005556 |
| Human Cytokeratin 8 | KRT8 | NM_002273 |
| Human Cytokeratin 10 | KRT10 | NM_000421 |
| Human Cytokeratin 13 | KRT13 | NM_153490 |
| Human Cytokeratin 14 | KRT14 | NM_000526 |
| Human Cytokeratin 15 | KRT15 | NM_002275 |
| Human Cytokeratin 16 | KRT16 | NM_005557 |
| Human Cytokeratin 17 | KRT17 | NM_000422 |
| Human Cytokeratin 18 | KRT18 | NM_199187 |
| Human Cytokeratin 19 | KRT19 | NM_002276 |

It should be noted that the hybridization probe of step b and d of the method described in the first embodiment (see Summary of the Invention) may be complementary to either the coding strand or the non-coding strand of the gene. Preferably, the probe is complementary to the coding strand (non-template strand). In a related embodiment, the probe is directed to the mRNA. If the probe is to be directed to the mRNA, it may be directed to splice junctions, which means, that the sequences are split in the DNA.

The term "a fraction thereof" is used to indicate that the maternal blood sample may be contacted directly with a ligand or a hybridization probe or that the maternal blood sample may be pre-processed such as to only comprise a fraction of the original maternal blood sample when being contacted with the ligand or hybridization probe. The maternal blood sample may e.g. be subject to concentration of its cells, a coagulation step or an enrichment step before being contacted with the ligand or hybridization probe.

In a preferred embodiment, the method comprises
a. Providing a maternal blood sample or a fraction thereof
b. Contacting the sample with
   i. a hybridization probe comprising at least 10 contiguous nucleotides complementary to a gene encoding human vimentin and/or
   ii. a ligand directed to human vimentin.

In another preferred embodiment, the method comprises
a. Providing a maternal blood sample or a fraction thereof
b. Contacting the sample with
   i. a hybridization probe comprising at least 10 contiguous nucleotides complementary to a gene encoding human cytokeratin 7 and/or
   ii. a ligand directed to human cytokeratin 7.

In a more preferred embodiment, the method comprises
a. providing a maternal blood sample or a fraction thereof
b. contacting the sample with
   i. a hybridization probe comprising at least 10 nucleotides complementary to a gene encoding CD105 and/or
   ii. a ligand directed to CD105 (SEQ ID NO: 1 or SEQ ID NO: 2) and
c. contacting the sample with
   i. a hybridization probe comprising at least 10 contiguous nucleotides complementary to a gene encoding cytokeratin 7 (SEQ ID NO: 7) and/or
   ii. a ligand directed to human cytokeratin 7 in done after the maternal blood sample has been contacted with an endothelial marker, in a preferred embodiment CD105.

In yet another preferred embodiment, the method comprises
a. Providing a maternal blood sample or a fraction thereof
b. Contacting the sample with
   i. a cross-reacting hybridization probe comprising at least 10 contiguous nucleotides complementary to the genes in the group consisting of a gene encoding human cytokeratin 1-6, 8, 10 and 13-19 and/or
   ii. A cross-reacting ligand directed to human cytokeratins 1-6, 8, and 13-19.

In this embodiment, the ligand can bind to multiple cytokeratins, i.e. cytokeratins 1-6, 8, 10 and 13-19. This cross reactivity can be achieved by directing the ligand to conserved (identical) regions of the cytokeratin. Likewise, cross reacting hybridisation probes can be designed by directing the probe to conserved (identical) regions of the genes encoding the mentioned cytokeratins.

In a preferred embodiment, the method comprises:
a. Providing a maternal blood sample or a fraction thereof
b. Contacting the sample with
   i. a hybridization probe comprising at least 10 nucleotides complementary to a gene encoding CD105 and/or
   ii. a ligand directed to CD105 and
c. Contacting the sample with
   i. a cross-reacting hybridization probe comprising at least 10 contiguous nucleotides complementary to the genes in the group consisting of a gene encoding human cytokeratin 1-6, 8, 10 and 13-19 and/or
   ii. A cross-reacting ligand directed to human cytokeratins 1-6, 8, and 13-19.

In still another embodiment, a mixture of hybridisation probes or ligands (one for each antigen or gene) are used as an alternative to a cross reacting hybridisation probe or cross reacting ligand.

In one such embodiment, the method comprises the steps of
a. Providing a maternal blood sample or a fraction thereof
b. contacting the sample with
   i. a hybridization probe comprising at least 10 nucleotides complementary to a gene encoding CD105 and/or
   ii. a ligand directed to CD105 and
c. Contacting the sample with
   i. A mixture of hybridization probes, comprising hybridisation probes comprising at least 10 contiguous nucleotides complementary to the genes in the group consisting of a gene encoding human cytokeratins 1-6, 8, 10 and 13-19, a hybridisation probe comprising at least 10 contiguous nucleotides complementary to a gene encoding human cytokeratin 7 and a hybridisation probe comprising at least 10 contiguous nucleotides complementary to a gene encoding human vimentin and/or
   ii. A mixture of ligands comprising a cross-reactive ligand directed to human cytokeratins 1-6, 8, 10 and 13-19, a ligand directed to human cytokeratin 7 and a ligand directed to human vimentin In a preferred embodiment cells reactive to both an endothelial (i.e. CD105) and epithelial marker (i.e. cytokeratin 7) is subsequently identified and selected for further analysis.

In a preferred embodiment step b preferably utilizes a hybridisation probe as described herein below and step d utilizes a ligand as described herein below.

Whole Blood Selection

In one embodiment, the maternal blood sample of step a of the method described in the first embodiment is whole blood, i.e. the blood has not been subjected to any fractionations before being contacted with a ligand directed to an endothelial cell marker or a hybridisation probe directed to a gene encoding an endothelial cell marker.

Fixation and Selective Lysis

In a preferred embodiment of the invention, the cells of the maternal blood sample are fixed as described in one embodiment of the invention. The number of maternal cells largely exceeds the number of foetal cells present in a maternal blood sample, thus it may be useful to include a step of enrichment whereby maternal cells are removed from the sample to be analysed. The enrichment step may be performed at any suitable time point during the procedure, most suitable as step after step a of the method described in the first embodiment. In order not to remove any foetal cells it is preferred that the enrichment step does not discriminate between different foetal nucleated cell types. A large fraction of the maternal cells in the blood sample is comprised by erythrocytes. Several methods of removing erythrocytes is known, and most convenient is erythrocyte lysis, which may be achieved by $NH_4Cl$ mediated lysis Thus, in a preferred embodiment, the maternal erythrocytes are selectively lysed immediately after fixation. Accordingly the method of identifying a fetal cell in a maternal blood sample comprises the steps of:
   a. Providing a maternal blood sample or a fraction thereof
   b. Enriching the fetal cells by subjecting said maternal blood sample to erythrocyte lysis
   c. Fixating the remaining cells,
   d. Contacting the sample with a hybridization probe comprising at least 10 contiguous nucleotides complementary to a gene encoding an endothelial cell marker or a ligand binding to an endothelial cell marker and
   e. enriching the cells specific for said endothelial cell marker
   f. Contacting the cells selected in b) demonstrating an endothelial phenotype with a hybridization probe comprising at least 10 contiguous nucleotides complementary to a gene encoding an epithelial cell marker or a ligand directed to an epithelial cell marker
   g. Detecting the cells with endothelial phenotype also binding the epithelial cell marker of step c)
   h. Optionally, diagnosing and/or predicting the genetic content of the cells detected in d)
wherein step b-e may be performed in any order, preferably in the order indicated above.

Permabilization

In yet another embodiment, the cells of the maternal blood sample is subjected to a permeabilization step before being contacted with ligands or hybridisation probes as described above. I.e. the permeabilixation step is performed before step b of the method described in the first embodiment. This step preferably comprises contacting the sample with methanol, acetone or saponine. Preferably, the permeabilizing agent is methanol. Accordingly the method of identifying a fetal cell in a maternal blood sample comprises the steps of:

a. Providing a maternal blood sample or a fraction thereof
b. Permeabilizing the cells of said maternal blood sample,
c. Contacting the sample with a hybridization probe comprising at least 10 contiguous nucleotides complementary to a gene encoding an endothelial cell marker or a ligand binding to an endothelial cell marker and
d. enriching the cells specific for said endothelial cell marker
e. Contacting the cells selected in b) demonstrating an endothelial phenotype with a hybridization probe comprising at least 10 contiguous nucleotides complementary to a gene encoding an epithelial cell marker or a ligand directed to an epithelial cell marker
f. Detecting the cells with endothelial phenotype also binding the epithelial cell marker of step c)
g. Optionally, diagnosing and/or predicting the genetic content of the cells detected in d)

wherein step b-e may be performed in any order

Positive Selection

Preferably, antigen dependent enrichment comprises contacting the maternal blood sample with antibodies directed to CD105 as described in the examples section and in one embodiment of the invention. I.e. in one embodiment step b of the method described in the first embodiment is an antigen dependent step.

In a preferred embodiment, the maternal blood sample is fixed, lysed and enriched using antibodies directed to CD105 before being contacted with ligands or hybridisation probes directed at epithelial cells (i.e. step d of the method described in the first embodiment).

Efficiency

A preferred embodiment of the present invention makes fetal cell identification commercially feasible, because it dramatically lowers the number of individual cells that has to be analysed for identification of fetal cells. The present invention reduces the number of cells in the sample 10 to 20 fold such that they can be analysed using automated scanning of about 20 to 30 slides. I.e. the invention not only provides fetal cell specific antigens for use in fetal cell identification. It also provides enrichment methods that dramatically reduce the number of cells that is to be analysed for fetal cell identification. The methods enables consistent identification of 0.1 to 1.1 fetal cells/ml of maternal blood sample and with the analysis of only 20 to 30 slides/$10^6$-$10^7$ total cells. The area of the slides that are covered by cells is typically 15 mm×15 mm further underscoring the efficiency of the method.

Hybridisation Probes

Hybridisation probes of step b and d of the method described in the first embodiment of the invention in the section "Summary of the Invention" are used as generally in the art and are typically DNA or RNA, preferably DNA. In preferred embodiments, the probes are modified with non-natural nucleotides that improve binding affinity and/or binding specificity. Preferred examples of such non-natural nucleotides are LNA (locked nucleic acids), TINA (twisted intercalating nucleic acids), PNA (peptide nucleic acid), INA (intercalating nucleic acids), morpholino and 2'O-substituted RNA monomers such as 2'O-methyl RNA monomers and 2'O-(2-methoxyethyl) RNA.

The length of the probes may be any suitable length, such as in the range of 10 to 200 nucleotides, preferably between 10 and 30 nucleotides, more preferably 15-25 nucleotides and preferably, the probe is fully complementary to the gene encoding encoding human cytokeratin 1, 2, 3, 4 (SEQ ID NO: 3), 5 (SEQ ID NO: 4), 6A (SEQ ID NO: 5), 6B (SEQ ID NO: 6), 7 (SEQ ID NO: 7), 8 (SEQ ID NO: 8), 10 (SEQ ID NO: 9), 13 (SEQ ID NO: 10 and SEQ ID NO: 11), 14, 15, 16, 17, 18 (SEQ ID NO: 12 and SEQ ID NO: 13) and 19, CD105 (SEQ ID NO: 1 and SEQ ID NO: 2) and/or human vimentin over the length of the probe.

In one embodiment the probe is at least 85% complementary to a gene encoding any of the proteins described in table 1-3, preferably of table 2, such as at least 90% complementary, for example at least 95% complementary over the length of the probe. The probe may be complementary to the DNA or the mRNA encoding said protein.

In one embodiment the probe is at least 85% complementary to the gene encoding human cytokeratin 1, 2, 3, 4 (SEQ ID NO: 3), 5 (SEQ ID NO: 4), 6A (SEQ ID NO 5), 6B (SEQ ID NO: 6), 7 (SEQ ID NO: 7), 8 (SEQ ID NO: 8), 10 (SEQ ID NO: 9), 13 (SEQ ID NO: 10 and SEQ ID NO: 11), 14, 15, 16, 17, 18 (SEQ ID NO: 12 and SEQ ID NO: 13) and 19, CD105 (SEQ ID NO 1 and SEQ ID NO: 2) and/or human vimentin, such as at least 90% complementary, for example at least 95% complementary over the length of the probe. The probe may be complementary to the DNA or mRNA encoding said protein.

In one preferred embodiment the probe is fully complementary to the gene encoding CD105 (SEQ ID NO: 1 and SEQ ID NO: 2) over the length of the probe. In another preferred embodiment the probe is fully complementary to the gene encoding CK18 (SEQ ID NO: 12 and SEQ ID NO 13) over the length of the probe.

In one embodiment the hybridization probes for use in step b of the method described in the first embodiment of the invention in the section "Summary of the Invention" may be selected from hybridization probes hybridizing to a nucleotide encoding a protein selected from the group consisting of: CD 105, Vimentin, VCAM, ICAM, VEGFR-1, VEGFR-2, VEGFR-3, PAI-1 and EPCR.

Most preferred is CD105 (SEQ ID NO: 1 and SEQ ID NO: 2).

In one embodiment the hybridization probes for use in step d of the method described in the first embodiment may be selected from hybridization probes hybridizing to a nucleotide encoding a protein selected from the group consisting of: CK1, CK2, CK3, CK4, CK5, CK6, CK7, CK8, CK10, CK13, CK14, CK15, CK16, CK17, CK18 and CK19.

Most preferred is CK18 (SEQ ID NO: 12 and SEQ ID NO: 13).

Reporter Dyes

The hybridization probes and ligands to be used according to the invention in step b and d of the method described in the first embodiment of the invention described in "Summary of the Invention" may comprise or preferably be linked to a reporter dye (also herein termed a label). Said hybridization probes or ligand are preferably covalently linked to a reported dye. The reporter dye is preferably a fluorescent reporter dye. Preferably, the reporter dye is selected from the group consisting of FAM™, TET™, JOE™, VIC™, SYBR® Green, 6 FAM, HEX, TET, TAMRA, JOE, ROX, Fluorescein, Cy3, Cy5, Cy5.5, Texas Red, Rhodamine, Rhodamine Green, Rhodamine Red, 6-CarboxyRhodamine 6G, Alexa Fluor, Oregon Green 488, Oregon Green 500 and Oregon Green 514.

In one embodiment, the hybridization probes also comprise a quenching dye. In a preferred embodiment, the quenching dye is selected from the group consisting of TAMRA™, Black Hole Quencher™, DABCYL, BHQ-1, BHQ-2, DDQ I, DDQ II and Eclipse Dark Quencher.

The use of reporter and quenching dye is desirable because it allows various kinds of quantifications in addition to identification.

Typically, the reporter dye and the quencher dye are located near each other in the hybridization probe, allowing light- or laser-induced fluorescence emitted by the reporter to be quenched by the quencher dye. When the oligonucleotide binds to a complementary template strand, the reporter dye and the quencher dye are separated from each other such that the quencher no longer quenches the signal from the reporter, i.e. hybridization can be detected.

Thus, in one embodiment, the hybridization probe is capable of forming a stem-loop structure, wherein the quencher and reporter dye are brought into proximity in the stem. In one embodiment, the oligonucleotide is a so-called molecular beacon. The quencher and the reporter are no longer in proximity, when the molecular beacon base pairs to a template strand. Therefore the laser-induced signal from the reporter dye is no longer quenched.

Instead of using a reporter dye and a quencher dye, a so-called FRET (fluorescence resonance energy transfer) pair comprising a donor fluorophor and an acceptor fluorophor may be used. When the donor fluorophor is excited by an external light source, it emits light at a wavelength, which excites the acceptor fluorophor, which in turn emits light at a different wavelength, which can be detected and measured. The energy is only transferred from the donor to the acceptor if the donor fluorophor and acceptor fluorophor are in close proximity.

Preferred FRET pairs include BFP-YFP, CFP-YFP, GFP-DsRed, GFP-Cy3, GFP-mOrange, YFP-RFP, FAM-ROX, FAM-Cy5, FAM-Hex, FAM-TAMRA and Cy3-Cy5.

In one embodiment of the present invention the hybridization probes and ligands to be used in step b of the method described in the first embodiment is preferably linked to a reporter dye, said reporter dye being different from the reporter dye linked to the hybridization probes and ligands to be used in step d of the same method.

Ligands

The ligand as used in the method of the invention in step b and d of the method described in the first embodiment is preferably an antibody, a peptide or an aptamer. A ligand as used in the method of the invention binds primarily to the cell(s) of interest, preferably with a higher affinity than binding to other cells. Thus preferably the ligand binds primarily to said endothelial cell marker or said epithelial cell marker.

The ligand may be an aptamer, Aptamers are nucleic acid based high-affinity ligands that bind to antigens such as proteins. They are typically identified using in vitro evolution techniques such as SELEX (systematic evolution of ligands by exponential enrichment). In SELEX, iterated rounds of selection and amplification of nucleic acids from an initial library is used for identification of high-affinity aptamers. Since the initial library is very large (e.g. $10^{14}$ different sequences) and sequences may be mutated during iterated rounds, identification of high affinity aptamers can now be done on a routine basis and such methods are known to the skilled man. Preferred aptamers are less than 50 nucleotides in length.

High affinity peptides may be generated using phage display. In phage display, a library of phages displaying peptides are selected against the target and subsequently amplified in an evolution process similar to SELEX. Various systems for phage display exist and the size of the peptide may be chosen to suit particular needs. In one embodiment, the peptides to be used with the method of the invention have a size of less than 50 amino acids.

Often the library is displayed at a scaffold, e.g. an antibody scaffold. Thus, phage display may be used to identify high affinity antibodies. Other in vitro evolution techniques for antibody generation involve mRNA display, ribosome display and covalent DNA display.

The ligand may also be an antibody. An antibody according to the invention is a polypeptide or protein capable of recognising and binding an antigen comprising at least one antigen binding site. Said antigen binding site preferably comprises at least one CDR. The antibody may be a naturally occurring antibody, a fragment of a naturally occurring antibody or a synthetic antibody.

The term "naturally occurring antibody" refers to heterotetrameric glycoproteins capable of recognising and binding an antigen and comprising two identical heavy (H) chains and two identical light (L) chains inter-connected by disulfide bonds. Each heavy chain comprises a heavy chain variable region (abbreviated herein as $V_H$) and a heavy chain constant region (abbreviated herein as $C_H$). Each light chain comprises a light chain variable region (abbreviated herein as $V_L$) and a light chain constant region (abbreviated herein as $C_L$). The $V_H$ and $V_L$ regions can be further subdivided into regions of hypervariability, termed complementarity determining regions (CDRs), interspersed with regions that are more conserved, termed framework regions (FRs). Antibodies may comprise several identical heterotetramers.

Antibodies may also be generated using immunization of suitable animals such as mice, rat, goat, rabbit, horse etc.

Antibodies used for the present invention may be either monoclonal or polyclonal. Methods of generating both types of antibodies are well known to the skilled artisan. In addition to in vitro evolution methods outlined above, monoclonal antibodies are typically prepared using hybridoma technology.

In a preferred embodiment the ligand is an antibody or an aptamer that recognizes and binds an antigen selected from the group consisting of:
CK1, CK2, CK3, CK4, CK5, CK6, CK7, CK8, CK10, CK13, CK14, CK15, CK16, CK17, CK18, CK19, CD105, Vimentin, VCAM, ICAM, VEGFR-1, VEGFR-2, VEGFR-3, PAI-1, EPCR, CD9, ITGA5, ITGB5, CDH11, CDH3, CPM, CD39, CD200, EPHB4 and PAR-1.

In a preferred embodiment the ligand for use in step b of the method described in the first embodiment of the invention in the section "Summary of the Invention" is selected from the group consisting of: CD 105, Vimentin, VCAM, ICAM, VEGFR-1, VEGFR-2, VEGFR-3, PAI-1 and EPCR.

Most preferred is CD105 (SEQ ID NO: 1 and SEQ ID NO: 2).

In a preferred embodiment the ligand for use in step d of the method described in the first embodiment of the invention in the section "Summary of the invention" is selected from the group consisting of: CK1, CK2, CK3, CK4, CK5, CK6, CK7, CK8, CK10, CK13, CK14, CK15, CK16, CK17, CK18 and CK19.

Most preferred is CK18 (SEQ ID NO: 12 and SEQ ID NO: 13).

Specificity of Ligands

Preferably the ligands for use in step b and d of the method described in the first embodiment bind specifically to fetal cells. When referring to specificity, what is meant is that the ligands have a higher binding affinity for fetal cells than for maternal cells. Binding affinity may be expressed in terms of a dissociation constant (kd) and specificity as a ratio between the kd of a given ligand for maternal cells and the kd of the same ligand for fetal cells. I.e. a ligand may have a kd of $10^{-5}$ M for maternal cells and $10^{-9}$ M for fetal cells. In this case, the specificity would be 10,000. However, since both fetal cells and maternal cells are not necessarily a homogenous population, specificity may also be expressed in terms of the fold of enrichment that can be achieved with a given ligand (as further described below).

In a preferred embodiment, the ligands are generated by the method of the present invention described herein below. I.e. the specificity of the ligands has been optimized.

Preferably, the method further comprises a step of identifying fetal cells of the sample and/or a step of enriching fetal cells of the sample. In a preferred embodiment, the step of enrichment is performed before the step of identification.

After enrichment and/or identification, a step of detection and a step of prediction and/or diagnosis are often performed.

Identification

When the method comprises a step of identification, one embodiment comprises detecting the presence of the ligand or the hybridization probe on or in the fetal cells (step e of the method described in the first embodiment).

Detection may be enabled by labeling the ligand or the hybridization probe with fluorescent dyes or other dyes suitable for detection. Thus, the method may e.g. be fluorescent in-situ hybridization (FISH). The probe may comprise a quencher as well as a fluorophor or a FRET pair as described above, which enables detection of hybridisation probes bound to their target sequences. Alternatively or additionally, probes binding to their targets are separated from non-binding probes by one or more washing steps.

Identification may also be done using immunostaining using a ligand such as an antibody.

Identification may be done using multicolor FISH or multicolor immunostaining. I.e. different hybridization probes with different fluorescent labels may be used simultaneously or two (or more) different antibodies with different fluorescent labels may be used simultaneously. They may both be specific for fetal cells or one may be specific for fetal cells and the other may be specific for maternal cells.

In one embodiment the identified fetal cell may be subjected to Laser Capture Microdissection (LCM).

Enrichment

In a preferred embodiment, a ligand dependent or hybridization probe dependent enrichment step is performed after the maternal sample has been contacted with the ligand or the hybridization probe i.e. step c of the method described in the first embodiment of the invention in the "Summary of the Invention". In one embodiment, enrichment may also be performed after step d of the method described in the first embodiment. For enrichment, a ligand is preferred over a hybridization probe.

The ligand used in step c of the method described in the first embodiment of the invention is preferably linked to a metal molecule, such as magnetic beads.

When referring to enrichment, what is meant is that the ratio of fetal cells to maternal cells of the sample is increased. The fold of enrichment is preferably more than 1000 fold, even more preferably more than 10,000 fold and most preferably more than 100,000 fold.

In another embodiment, the fold of enrichment is selected from the group consisting of more than 10 fold, more than 100 fold, more than 1000 fold, more than 10,000 fold, more than 100,000 fold and more than 1,000,000 fold.

The basis of the enrichment is the identified mRNAs preferentially expressed in fetal cells and proteins encoded by the mRNAs.

As will be clear to the person skilled in the art, additional antigen dependent enrichment steps based on ligands (or antigens) known from the prior art may be performed. Examples of such antigens known from the prior art are: CD34, Tra, Oct1, Crypto1, SSEA1, CD29, CD33, CD146 and CD166.

As described above in relation to e.g. CD105, an enrichment step may also be performed before the maternal sample has been contacted with the ligand or the hybridization probe, i.e. before step b of the method described in the first embodiment.

Flow-Based Sorting

In a preferred embodiment, the enrichment is done using fluorescent activated cell sorting (FACS). Thus, the ligand is fluorescently labelled which allows FACS. FACS and suitable labels are well known to the skilled artisan and examples have been given above.

As an alternative to FACS, microfluidic device cell sorting may be used.

Immobilization

In another preferred embodiment, enrichment is done using immobilization of the ligands. The ligands for use in step b and/or d of the method described in the first embodiment of the invention in the "Summary of the Invention" may e.g. by immobilized on beads such as magnetic beads, sepharose beads, agarose beads etc. When the ligands and cells bound thereto are immobilized, unbound cells can be washed of the beads. Such washing process may be performed in batch or on a column. After enrichment (fractionation), bound cells can be eluted using high or low salt, cleavable linkers, low or high pH, denaturing agents etc. More preferably, bound cells are eluted using competitive elution with soluble antigens or secondary ligands binding to the fetal cell specific ligands, e.g. antibodies directed to the fixed part of the ligand used for immobilization.

A preferred method of enrichment is MACS (immunomagnetic cell sorting), where the ligands are immobilized on magnetic beads. I.e. cells bound to the ligands can be separated from non-binders by selecting the particles using magnetism.

In a preferred embodiment enrichment in step b of the method described in the first embodiment is performed using CD105 immobilized on magnetic beads.

Negative Selection Using Antigens

Ligands that bind specifically to maternal cells may also in one embodiment be used for enrichment. Thus, in a preferred embodiment, the method further comprises a step of contacting the sample with a maternal cell specific ligand directed to a maternal antigen. This step may be performed at any time suitable such as before step b of the method described in first embodiment. After contacting the sample with a maternal cell specific ligand, enrichment may e.g. be done using FACS, MACS, microfluidics or immobilization as described above.

Preferably, the ligand is selected from the group consisting of ligands that bind to antigens encoded by mRNAs preferentially expressed in maternal blood cells but not in fetal cells as identified by the present inventors.

As will be clear to the person skilled in the art, additional antigen dependent enrichment steps (negative selections) based on ligands (or antigens) known from the prior art may be used. Thus in one embodiment, an additional antigen dependent enrichment step is performed, where the ligand is selected from the group consisting of ligands that bind to maternal specific antigens known from the prior art such as CD45, HLA-A, HLA-B or antibodies selected from the group consisting of HLe-1, M3 and L4.

A preferred cell type marker for negative selection is CD45 also known as leukocyte common antigen. CD45 is a transmembrane protein expressed by all differentiated hematopoietic cells except erythrocytes and plasma cells. The CD45 protein exists in different forms which are all produced from a single complex gene giving rise to eight different mature mRNAs and resulting in eight different protein products. It is expressed on all leukocytes but not on other cells, and thus functions as a pan-leukocute marker including the different and diverse types of leukocytes (or white blood cells) such as neutrophils, eosinophils, basophils, lymphocyte (B and T cells), monocytes and macrophageds.

Due to the expression of CD45 on a large majority of the nucleated cells present in maternal blood a negative selection using the CD45 marker is preferred. Following depletion of CD45 positive cells, the CD45 negative cells of the sample is collected. Such depletion and collection can be performed by any suitable method known in the art.

In one embodiment the cells present in the maternal blood sample or a fragment thereof is counterstained using a CD45 marker at any suitable time point thereby identifying the maternal cells present in the sample. The CD45 negative cells of the sample may then be collected. Such a counterstain and collection may be performed using any suitable method known in the art.

HLA

The human leukocyte antigens, part of the human major histocompatibility complex (MHC) is responsible for cell-surface antigen-presenting proteins and many other genes.

Two classes of the human leukocyte antigens are present, class I antigens (A, B & C) and class II antigens (DR, DP, & DQ) which have different functions. Both classes include a high number of variable alleles.

HLA genes not expressed by fetal cells may be used for depletion of maternal cells in the sample. I.e. the maternal blood sample or fraction thereof present in step a of the method described in the first embodiment may be subjected to antigens directed at HLA genes.

Other Enrichment Methods

Additional enrichment methods that do not use antigen specific ligands may also be used.

A preferred additional method of enrichment is lysis of erythrocytes such as NH$_4$Cl mediated lysis, which allows selective lysis of erythrocytes leaving nucleated cells intact. This method is known by a person skilled in the art. In a preferred embodiment lysis of erythrocytes is performed before step b of the method described in the first embodiment. For NH$_4$Cl mediated lysis preferably a concentration of 0.1-0.2 mM NH$_4$Cl is used, such as 0.14-0.18 mM NH$_4$Cl more preferably mM 0.15-0.17 NH$_4$Cl.

Also the methods of fixation and selective lysis described herein above may be used for enrichment.

The sample may also be subjected to initial separation based on size or density, such as by Ficoll-Hypaque density gradient centrifugation. This results in production of a supernatant layer, which contains platelets; a mononuclear cell layer; and an agglutinated pellet which contains non-nucleated erythrocytes and granulocytes. The mononuclear layer is separated from the other layers to produce a maternal sample enriched in fetal cells.

Also physical properties of cells, such as but not exclusively charge, may be utilized for enrichment.

Sedimentation

The cells present in the blood sample may be enriched by sedimentation, where the majority of cells present in the sample are allowed to sediment. The blood sample may prior to sedimentation be diluted in a suitable solution, such as 0.15 M NaCl. The sedimentation may continue until total sedimentation has occurred, such as for at least 5 hours, or preferably overnight.

Preferably the sample is allowed to sediment at a temperature below room temperature, such as at a temperature of less than 15° C., such as less than 10° C. or 8° C. or 6° C., preferably at a temperature of 2-8° C. or around 4° C.

A minor population of cells with a low density may not sediment and may be isolated by mild pre-fixation as described, such as in 0.5% paraformaldehyde followed by centrifugation.

Combining Ligands and Enrichment Methods

As will be understood, the various ligands and enrichment methods may be combined. Thus, 1, 2, 3 or more fetal cell specific ligands directed at cells with endothelial phenotype (i.e. endothelial cell markers) may be used at the same time or in succession. Likewise iterated enrichments using respectively fetal cell specific ligands and maternal specific ligands may be used.

The Sample

It is desirable to obtain as large a maternal blood sample as possible in order to increase the total number of fetal cells. Accordingly, the size of the maternal blood sample of step a in the method described in the first embodiment is preferably in the range of 0.5 to 50 ml, such as in the range of 1 to 40 ml, such as from 5 to 35 ml or 10 to 30 ml.

The maternal blood sample provided is preferably obtained from a pregnant woman between 5-24 or 6-20 weeks of gestation, more preferably between 7-16, or 8-12 weeks of gestation.

Dilution—Concentration

Also, according to the invention the sample may be diluted or concentrated at anytime during the method. The sample may be diluted at least 1.5 times, such as twice, more preferred at least three times, such as five times by adding isotonic buffers, such as saline solutions, phosphate buffered saline solutions, PBS, and/or suitable growth media, such as basal media, and tissues growth media. A method step may include dilution of a sample by addition of various components allocated for the specific method step.

For carrying out the method it may for the feasibility of the different method steps be advantageous to concentrate the sample e.g. to reduce the volume without removing any cells. The sample volume may be decreased to less than 80%, such as 70, or 60 or 50% of the original sample volume, or even preferable to less than 40%, such as 25% of the original sample volume. A concentration step may be centrifugation. The method may according to the invention comprise one or more concentration steps. Centrifugation is a preferred method for concentrating the cells. In order to avoid damages of cells a mild centrifugation is preferred, such as 300 g for 10 minutes.

Detection and Diagnosis

Preferably, the method of the invention may be used for prenatal detection and prediction and/or diagnosis (i.e. step e and f of the method described in the first embodiment). Thus, an identified cell may be subject to detection and prediction and/or diagnosis or a maternal blood sample enriched for fetal cells may be subjected to detection and prediction and/or diagnosis.

In one embodiment, fetal proteins are made available for detection e.g. via immunoblotting, protein sequencing or mass spectrometry.

In another preferred embodiment, detection and/or diagnosis comprises a step of making fetal DNA or RNA available for detection.

Preferred detection methods of step e of the method described in the first embodiment are FISH (fluorescent in situ hybridization), northern blotting, southern blotting, DNA/RNA sequencing, microarray analysis and amplification. Such methods may be used to detect the presence of specific sequences that indicate a certain condition, e.g. pre-natal disease or predisposition to a certain disease. The methods may also be used to detect a chromosomal aneuploidy such as trisomy 13, trisomy 18 or trisomy 21. The detection methods can also be used to determine the gender of the fetus by detecting Y specific sequences.

In an alternative embodiment, the number of fetal cells in the sample is compared to a standard number. Increased numbers of fetal cells in the sample may indicate that the pregnancy is at risk. The number of fetal cells in the sample (as well as in a control sample) can be estimated using e.g. FACS.

Identification of Specific Ligands One embodiment of the invention is a method of identifying a fetal cell specific ligand comprising the steps:
 a) Providing a library of fetal cell specific ligand candidates
 b) Providing a pool of maternal cells
 c) Contacting the library of step a with the maternal cells of step b
 d) Selecting ligands that do not bind to the maternal cells to generate a library depleted for ligands that bind maternal cells In a preferred embodiment, the method further comprises the steps of
 e) Contacting the library of step a or the library of step d with a fetal cell
 f) Selecting ligands that bind to the fetal cell to generate a library that is enriched in ligands that bind to fetal cells, but not maternal cells It should be clear that one cell suffices for selection of the ligands of step f, but that more fetal cells may obviously be used.

In one embodiment the identified specific ligands are selected so that it is ensured that the ligands are directed to epithelial cells of placental origin.

Steps b-f may be carried out by the steps of
 g) Providing a maternal blood sample
 h) Contacting the library with a maternal blood sample
 i) Selecting ligands that bind to the fetal cells by removing individual fetal cells, which have been identified by FISH-demonstration of a Y chromosome and/or which have been identified by the method of fifth aspect of the invention, and collecting the ligands solely from these cells.

The maternal blood sample may have been enriched for fetal cells.

In a preferred embodiment, the method further comprises:
 j) multiplying/amplifying the selected ligands such as to prepare an amplified library for additional selections against fetal cells and/or against maternal cells.

As will be clear, multiple rounds of selection and amplification may be performed to identify the very best ligands.

In another embodiment the method of identifying a fetal cell specific ligand are performed as described in Example 1 of PCT/DK2010/050002.

The library of fetal cell specific ligand candidates may be a library of antibodies or peptides displayed on phages (phage display), mRNA (ribosome display or mRNA display) or on DNA (covalent display or plasmid panning). The library may also be a library of DNA or RNA oligonucleotides for the identification of aptamers.

The term "candidates" is used to imply that the compounds of the library do not necessarily bind to fetal cells. They are to be tested for binding for the identification of fetal cell specific ligands.

In one embodiment, the library of fetal cell specific ligand candidates is a fully random library. In such case, the library may first be iteratively selected against fetal cells and amplified, before counter selection (negative selection) against maternal cells is performed.

In another embodiment, the library of fetal cell specific ligand candidates is based upon known ligands of fetal cells. Such library may e.g. be created by displaying an antibody that binds to fetal cells on a phage and mutagenesis of the gene encoding the antibody to create a library. In such case, mutagenesis may improve specificity while retaining or even improving affinity for fetal cells.

In one embodiment, the ligand binds to an antigen encoded by a gene selected from the group consisting of consisting human cytokeratin 1, 4-6, 8, 10, 13, 18 and 19, human cytokeratin 7 and human vimentin. Thus affinity and/or specificity of the ligands are optimized using the method outlined above.

Fetal Cell Specific Ligands and Hybridization Probes

In one embodiment of the invention the endothelial specific ligand and hybridisation probes of step b of the method described in the first embodiment of the present invention may be selected from the group consisting of:
 i. a ligand directed to an antigen selected from the group consisting of CD105, Vimentin, VCAM, ICAM, VEGFR-1, VEGFR-2, VEGFR-3, PAI-1, EPCR and
 ii. a hybridization probe directed to nucleic acid comprising at least 10 nucleotides of a gene selected from the group consisting of a gene encoding CD105, Vimentin, VCAM, ICAM, VEGFR-1, VEGFR-2, VEGFR-3, PAI-1, EPCR In one embodiment of the invention the epithelial specific ligand and hybridisation probes of step d of the method described in the first embodiment of the present invention may be selected from the group consisting of:
 i. a ligand directed to an antigen selected from the group consisting of human CK1 CK1, CK2, CK3, CK4, CK5, CK6, CK7, CK8, CK10, CK13, CK14, CK15, CK16, CK17, CK18 and CK19 and
 ii. a hybridisation probe directed to nucleic acid comprising at least 10 nucleotides of a gene selected from the group consisting of a gene encoding CK1, CK2, CK3, CK4, CK5, CK6, CK7, CK8, CK10, CK13, CK14, CK15, CK16, CK17, CK18 and CK19.

In one embodiment the fetal cell specific ligand and hybridisation probe is selected from the group consisting of: CD105 and CK18.

In one embodiment, the ligand or the hybridisation probe is characteristic in that it enables 90% correct selection of cells in a test sample comprising 99.9% maternal cells and 0.1% fetal cells. I.e. when referring to 90% correct identification, what is meant herein is that when performing the selection with the test sample and with the ligand, 90 fetal cells will be collected for each 10 maternal cells and likewise for better/worse correctness. A preferred selection method is MACS. More preferred is a ligand that enables 95% correct selection, 98% correct selection or even more preferred 99% correct cell selection. Since a maternal blood sample has a very low abundance of fetal cells, it is even more preferred that the ligand enables 99.9%, 99.99% or 99.999% correct cell selection from a test sample as described above.

Preferably, the ligands are aptamers, peptides or antibodies. Most preferred are antibodies.

The ligands are preferably identified using the method described herein above or in PCT/DK2010/050002 such as to have an improved specificity.

In one embodiment of the invention the ligands or hybridization probes of the identified using the method described herein above or in PCT/DK2010/050002 are used for enriching a maternal blood sample for fetal cells or for identifying fetal cells in a maternal blood sample. Preferably use of the ligands or the hybridization probes is as described herein above.

Also provided is a kit comprising a ligand or a hybridization probe as described herein above and instructions for use.

Preferably, the kit comprises a first ligand for enrichment and a second ligand and/or a hybridization probe for identification. More preferably, the kit comprises a first ligand being an endothelial cell marker and a second ligand and/or hybridization probe being an epithelial marker. The endothelial cell marker is used for enrichment of the fetal cells and the epithelial marker is used for identification of the fetal cells present in the sample which contain both endothelial and epithelial phenotype.

In a preferred embodiment, the kit also comprises a fixation buffer and a lysis buffer as described herein above in the section "fixation and selective lysis".

In one embodiment of the invention the ligands or hybridization probes is used for identification of further fetal cell specific ligands. In a preferred embodiment of this use, the ligands and/or hybridization probes are used in the method described herein above or in PCT/DK2010/050002.

One aspect of the invention is a fetal cell identified by the method described herein above. Said cell is characteristic by its expression of a marker selected from the group of human cytokeratins 1, 2, 3, 4 (SEQ ID NO: 3), 5 (SEQ ID NO: 4), 6A (SEQ ID NO: 5), 6B (SEQ ID NO: 6), 7 (SEQ ID NO: 7), 8 (SEQ ID NO: 8), 10 (SEQ ID NO: 9), 13 (SEQ ID NO: 10 and SEQ ID NO: 11), 14, 15, 16, 17, 18 (SEQ ID NO: 12 and SEQ ID NO: 13), and 19 human vimentin and CD105 (SEQ ID NO: 1 and SEQ ID NO: 2) and can be distinguished from other cells by the expression of CD105 or vimentin and/or co-expression of CD105 or vimentin and cytokeratins. Preferably, the fetal cell has been isolated or identified e.g. as described in other aspects of this invention, and is not present in the human body.

One aspect of the invention is the use of the fetal cell identified by the method described herein above for detection and diagnosis as described above or for the generation of further fetal cell specific ligands e.g. as described in the section "identification of specific ligands".

Yet another aspect is a kit comprising
a.
  i. a hybridization probe comprising at least 10 contiguous nucleotides complementary to a gene encoding an epithelial cell marker or
  ii. a ligand directed to an epithelial cell marker.

b.
  i. a hybridization probe comprising at least 10 contiguous nucleotides complementary to a gene encoding an endothelial cell marker or
  ii. a ligand directed to an endothelial cell marker
and instructions for use.

Pre-Natal Gender Determination

The isolated fetal cell according to the present invention may further be used for determination of gender of the foetus, either by use of male specific probes or by employing antigen binding members identified by the method described herein for the detection of foetal cells, followed by suitable methods for determination of gender known to a person skilled in the art.

Prenatal Diagnosis of Chromosomal Abnormality

In parallel to determination of gender, the invention further relates to methods for determination of chromosomal abnormalities by detection of foetal cells based on antigens or binding member recognising said foetal cell antigens isolated or identified based on the present invention. Such methods of determination of chromosomal abnormalities relates to the detection of such as aneuploidy, translocation, unbalanced translocation, rearrangement, subtelomeric rearrangement, unbalance chromosomal rearrangement, unbalance subtelomeric rearrangement, deletion, inversions, unbalanced inversions, duplication and telomere instability and or shortening. The chromosomal abnormality may further be such as single nucleotide substitution, micro deletion, micro-insertion, short deletions, short insertion, multinucleotide changes, DNA methylation and/or loss of imprint. (LOI) In a preferred embodiment chromosomal aneuploidy is a complete and/or partial trisomy. Such as trisomy 21, trisomy 18, trisomy 13, trisomy 16 and/or XXX and other sex chromosome abnormalties. Alternatively the aneuploidy is a complete and/or partial monosomy, such as monosomy X, monosomy 21, monosomy 22, monosomy 16 and/or monosomy 15.

DNA hybridisation techniques may be used for determination of gender or determination of chromosomal abnormalities. Techniques known in the art includes methods such as fluorescent in situ hybridization (FISH), primed in situ labeling (PRINS), quantitative FISH (Q-FISH) and multi-color-banding (MCB). Fluorescence in situ hybridization (FISH) makes use of molecular probes labelled as described above with e.g. a fluorescence. A probe corresponding to a gene or DNA sequence is used and shows a signal under a microscope at a specific locus in a nucleus. The FISH technique may be applied to interphase cells and may confirm the presence of an euploid or an aneuploid of chromosomes X, Y, 13, 15, 18, 21. FISH is useful for identifying abnormal numbers of chromosomes such as trisomies and monosomies and may, when probes are available for specific regions of chromosomes, be used to determine if deletions, translocations, or duplications are present.

As an alternative to the above mentioned hybridisation techniques PCR methods may be used for determining chromosomal abnormalities. This would require initial isolation of the few fetal cells. PCR methods according to the invention includes suitable method known in the art, capable of detecting abnormalities as trisomies etc. as described above. PCR methods may further be employed for determination of minor abnormalities, such as small deletions of mutation in specific genes. Quantitative fluorescent PCR (QF-PCR) is an example of such methods suitable for detection of for example trisomy 13, 18, 21, triploidies, double trisomies as well as X and Y aneuploidies (V. Cirigliano, 2004). By the design of suitable primers for minor but none the less severe chromosomal abnormalities PCR methods may be used for determination of disease such as for example Cystic Fibrosis which is often caused by a 3 bp deletion in the Cystic Fibrosis Gene leading to a protein which lacks a critical phenylalanine amino acid.

The foetal cells may as described above be a stem cell. Stem cells come in different varieties, relating to when and where they are produced during development, and how versatile they are. The foetal stem cells detected may be of any type, such as embryonic, or somatic, being pluripotent or multipotent.

Use of Stem Cells.

By applying the technology described herein, foetal stem cells may be isolated from a maternal blood samples by use of a binding member, antibody or antibody fragment recognising said foetal cell antigen according to the invention. Stem cells can produce more stem cells and they can be used to generate specialized cell types such as nerve, blood or liver cells. Depending on the types of stem cells isolated the cells may have varying application in the development of cells of specific cell types or tissue. Pluripotent stem cells may give rise to any cell type whereas multipotent stem cells may give rise to a more limited number of cell types. For example, blood-forming (haematopoietic) stem cells may be capable of forming all types of blood cells, whereas mesenchymal stem cells are capable of forming mesenchymal cells.

Stem cells, especially pluripotent stem cells may be used for treatment of a variety of disease. Pluripotent stem cells are traditionally embryonic stem cells, which due to ethical considerations are of limited availability. The possibility of using stem cells isolated from a maternal blood sample is an attractive alternative. Pluripotent stem cells may be used for treatment of a plurality of diseases for which conventional methods does not provide suitable treatment.

REFERENCES

Gussin H A, Sharma A K, Elias S.>>Culture of endothelial cells isolated from maternal blood using anti-CD105 and CD133.<<*Prenat Diagn,* 2004: March; 24(3):189-93.

EXAMPLES

Example 1

Preparation of Blood Samples

Peripheral blood samples of 24 ml were obtained from pregnant women 11 to 14 week's gestational age. Blood samples were drawn before an invasive procedure and after informed consent. All blood samples were collected in heparinized tubes and processed immediately after they were collected.

In addition to the heparin blood, 5 ml of blood was drawn into EDTA tubes. This blood was used for fetal gender analysis. The gender of the fetus was determined by real time PCR of free fetal DNA using γ-chromosome specific genes. Only blood samples from male pregnancies were processed further.

Fixation

For each sample 3 ml of whole blood was aliquoted into pre-coated 50 ml centrifugation tubes (8 tubes per sample) using pre-coated pipettes (pre-coating buffer was 2% BSA in PBS w/o $Ca^{2+}$ and $Mg^{2+}$). Two ml of 10% formaldehyde in PBS was added to each tube using pre-coated pipettes. After careful mixing, the blood was fixed for 10 minutes at room temperature.

Selective Lysis

After fixation, 30 ml of 0.12% Triton X-100 in PBS (w/o Ca2+ and Mg2+) was added to each tube. The tubes were inverted 3 times, and the red blood cells were lysed for 45 minutes at room temperature. Following lysis, 15 ml cold (4° C.) 2% BSA in PBS (w/o Ca2+ and Mg2+) was added to each tube. After mixing by inverting the tubes twice, unlysed cells were pelleted by centrifugation at 500 g for 15 minutes at 4° C. After removing the supernatant, cells were re-suspended in 10 ml of 4° C. cold PBS (w/o Ca2+ and Mg2+), and stored overnight at 4° C.

Permeabilization

Samples were permeabilized by adding 10 ml of cold (−20° C.) methanol followed by an incubation at 4° C. for 10 minutes. After centrifugation at 500 g for 10 minutes, the cell pellets were pooled into 2 tubes using pre-coated pipettes. The empty tubes were rinsed with 1 ml of cold MASC buffer (PBS, 0.5% BSA, 2 mM EDTA). The pooled cells were then transferred to two pre-coated 15 ml tubes and centrifuged at 500 g for 10 minutes. After removal of the supernatant, the cells in each tube were re-suspended in 500 μl MACS buffer.

Positive Selection using CD105 Microbeads and MACS.

To 500 μl cell suspension 130 μl of CD105 microbeads (Miltenyi) were added and the cell suspension was incubated for 60 minutes at 4° C. The cells were then washed by adding 6 ml of cold MACS buffer followed by a centrifugation for 10 minutes at 500 g. The supernatant was removed and the cells re-suspended in 2 ml of cold MACS buffer.

The CD105 labeled cell suspension was applied to a pre-washed LD column (Miltenyi) already in place on the magnet and stacked on top of a pre-washed MS column (Miltenyi). When the cells had run through the LD column, it was washed twice with 2 ml of cold MACS buffer. The MS column was washed with 1 ml of cold MACS buffer. The LD column was then removed from the magnet, placed on a pre-coated 15 ml tube, and the cells were eluted by applying 2 times 5 ml of cold MACS buffer. The first 5 ml of buffer ran through the column without applying a plunger. The second 5 ml of buffer was forced through the column by applying a plunger. The MS column was then removed from the magnet and placed on the collection tube. The cells were eluted the same way as for the LD column using 2 times 1 ml of cold MACS buffer instead of 2 times 5 ml of buffer. The collection tube was centrifuged at 500 g for 10 minutes. The supernatant was discarded and the cell pellet was re-suspended in cold MACS buffer. The cell suspension was then placed on poly-lysine coated slides, and the slides were air-dried (overnight) before further analysis.

Identification of Male Fetal Cells by X- and Y-Chromosome Specific FISH and Automated Scanning.

Before hybridization, slides were rinsed in PBS for 5 minutes and dehydrated for 3 minutes each in 60%, 80% and 99.9% ethanol. The chromosome-specific repeat DXZ1 probe CEP X alpha satellite DNA labeled with spectrum green and DYZ1 probe CEP Y satellite III labeled with spectrum orange (Abbott Molecular) were used for this analysis. Hybridization mixtures containing both probes were prepared by mixing 1 part of the X-probe, 1 part of the Y-probe, 1 part of distilled water and 7 parts of hybridization buffer. Fifteen μl of hybridization mixture were added and covered by a 24×24 mm cover slip. The cover slips were sealed with rubber cement, and the DNAs denatured on a hot plate at 83.5° C. for 7 minutes and hybridized overnight in a humidified atmosphere at 42° C. Hybridized slides were washed for 2 minutes at 73° C. in 0.4×SSC with 0.3% Tween 20 and for 1 minute at room temperature in 2×SSC with 0.1% Tween 20. The slides were then mounted in Vectashield with DAPI.

Cells containing a red FISH signal located in a DAPI stained nucleus were identified by automatic scanning using two different types of scanners. The MDS (version 5.8.0) slide scanning system originally developed by Applied Imaging, and the MetaCyte scanning system developed by Metasystems. With the MDS scanning system, slides were scanned at 20× magnification using scan function 5. With MetaCyte, slides were scanned at 10× magnification using a classifier developed and optimized in-house for detection of true Spectrum Orange FISH signals. After scanning, cells identified by the scanner were inspected visually by automatic relocation. Cells that had one green X signal and one orange Y-signal significantly bigger than the X-signal were classified as male fetal cells.

Antibody Staining of Male Fetal Cells.

Fetal cells were stained with the following antibodies used individually. Pan Cytokeratin (product no. C2562, Sigma-Aldrich). Cytokeratin 7 (product no. M7018, DAKO Cytomation) and Vimentin (product no. V2258, Sigma-Aldrich). The anti-pan cytokeratin antibody recognizes human cytokeratin 1, 4-6, 8, 10, 13, 18 and 19. The anti-cytokeratin 7 antibody recognizes human cytokeratin 7, and the anti-vimentin antibody recognizes an epitope of human vimentin that is not detected in human lymphoid cells. All three antibodies are mouse monoclonals isotype IgG1, IgG2 (cytokeratins) or IgM (vimentin).

After air drying, slides were re-hydrated in 4×SSC in 10 minutes, then pre-incubated for 30 minutes at room temperature with 100 μl blocking buffer consisting of 4×SSC containing 10% normal goat serum, 1% BSA and 0.5% blocking reagent (Roche) or 100 μl Imaging Enhancer (Molecular Probes). Slides were then incubated for 60 minutes at room temperature with 100 μl primary antibody diluted 1:50 in blocking buffer. After antibody incubation, slides were washed 3 times for 5 minutes in 4×SSC. For detection, slides were incubated for 30 minutes at room temperature with 100 μl AlexaFluor-488 conjugated rabbit anti-mouse IgG (cytokeratins) or IgM (vimentin) (Molecular Probes) diluted 1:200 in blocking buffer, washed 3 times 5 minutes in 4×SSC and then incubated for 30 minutes at room temperature with 100 μl AlexaFluor-488 conjugated goat anti-rabbit Ig (Molecular Probes) diluted 1:200 in blocking buffer. After washing two times for 5 minutes in 4×SSC and once for 5 minutes in 2×SSC, slides were mounted in Vectashield with DAPI (Vector Laboratories).

Vimentin Antibody Staining Following Pan Cytokeratin Staining.

The coverslips were removed by washing in 4×SSC for 10 minutes. The slides were then rinsed in 4×SSC for 5 minutes and incubated for 30 minutes with 100 μl blocking buffer or Imaging Enhancer as described above. Slides were then incubated for 60 minutes at room temperature with 100 μl anti-vimentin antibody diluted 1:50 in blocking buffer. After antibody incubation, slides were washed 3 times for 5 minutes in 4×SSC. For detection, slides were incubated for 30 minutes at room temperature with 100 μl AlexaFluor-555 conjugated rabbit anti-mouse IgM diluted 1:200 in blocking buffer. After washing 2 times for 5 minutes in 4×SSC and once for 5 minutes in 2×SSC, slides were mounted in Vectashield with DAPI.

Antibody stained slides were placed in the scanning microscope and fetal cells were inspected visually for positive or negative staining by automatic relocation.

Experimental Results of Example 1.

Figure 2:
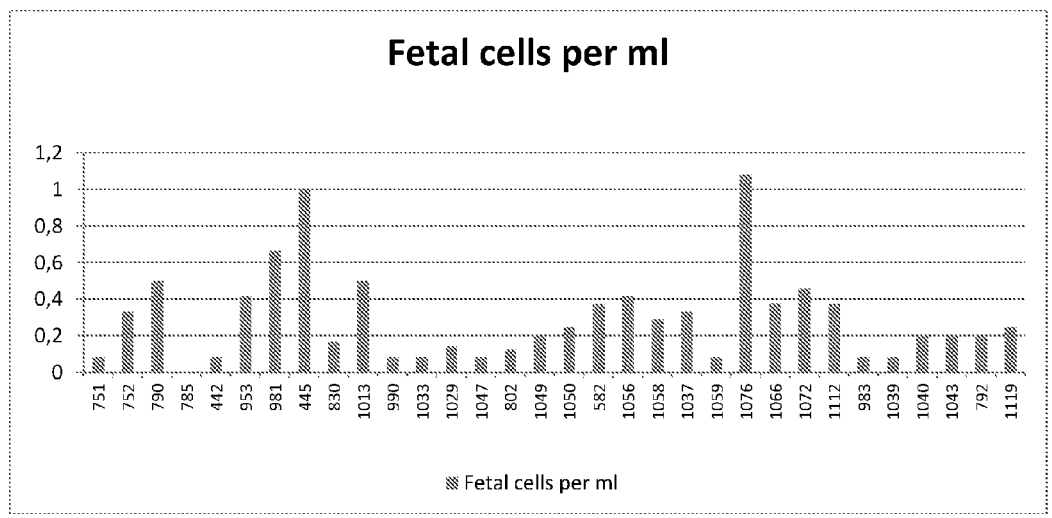
FIG. 2. Frequency of fetal cell per ml of maternal blood.
Figure 3:
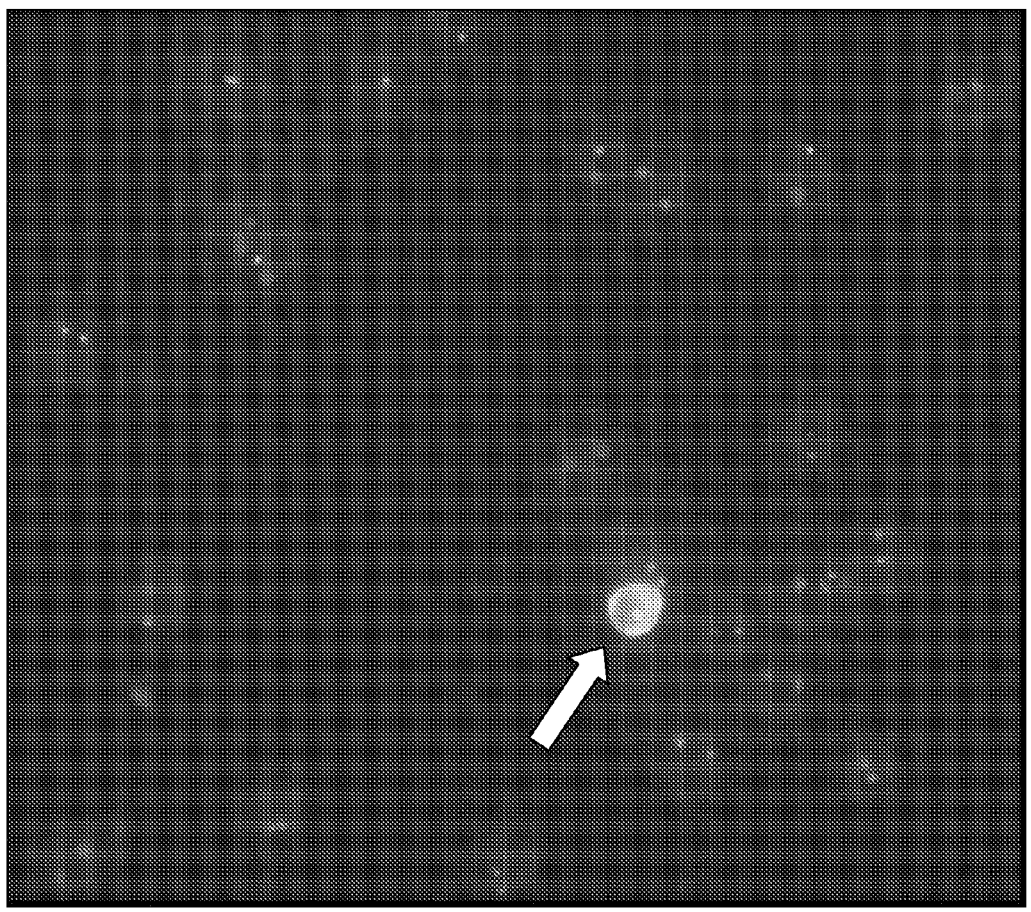
FIG. 3. Fetal cell showing pan cytokeratin staining. The arrow indicates the fetal cell.
Figure 4:
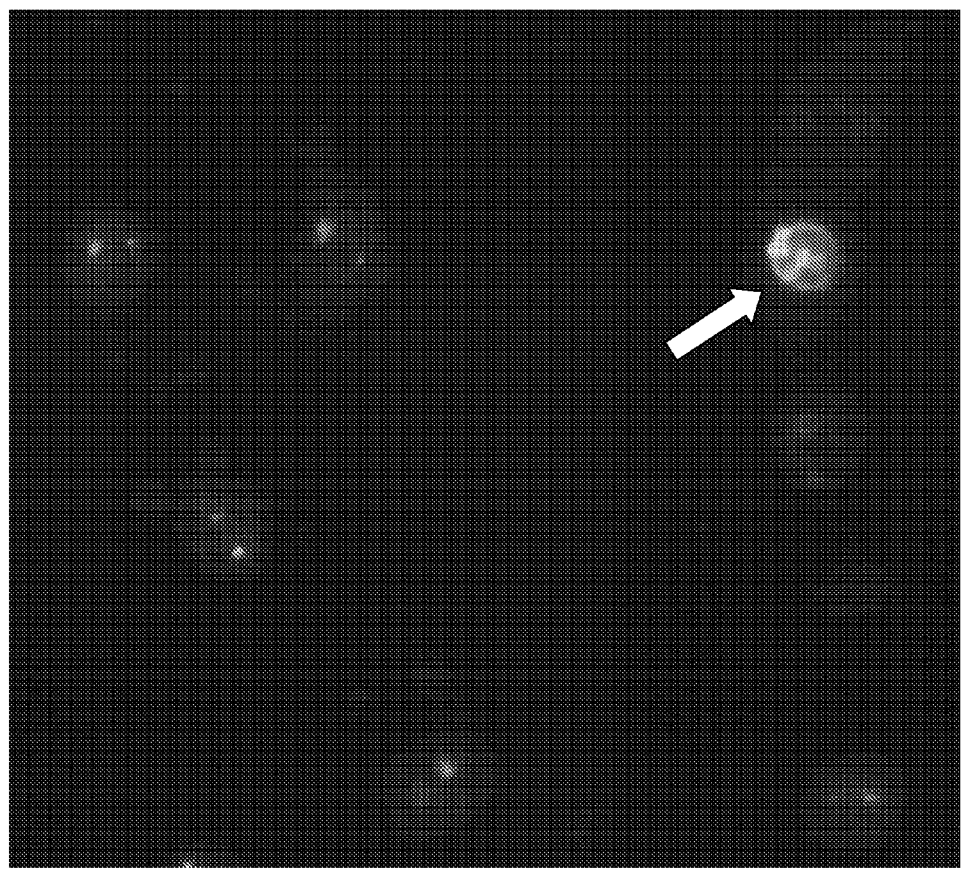
FIG. 4. Fetal cell showing cytokeratin 7 staining. The arrow indicates the fetal cell.
Figure 5:
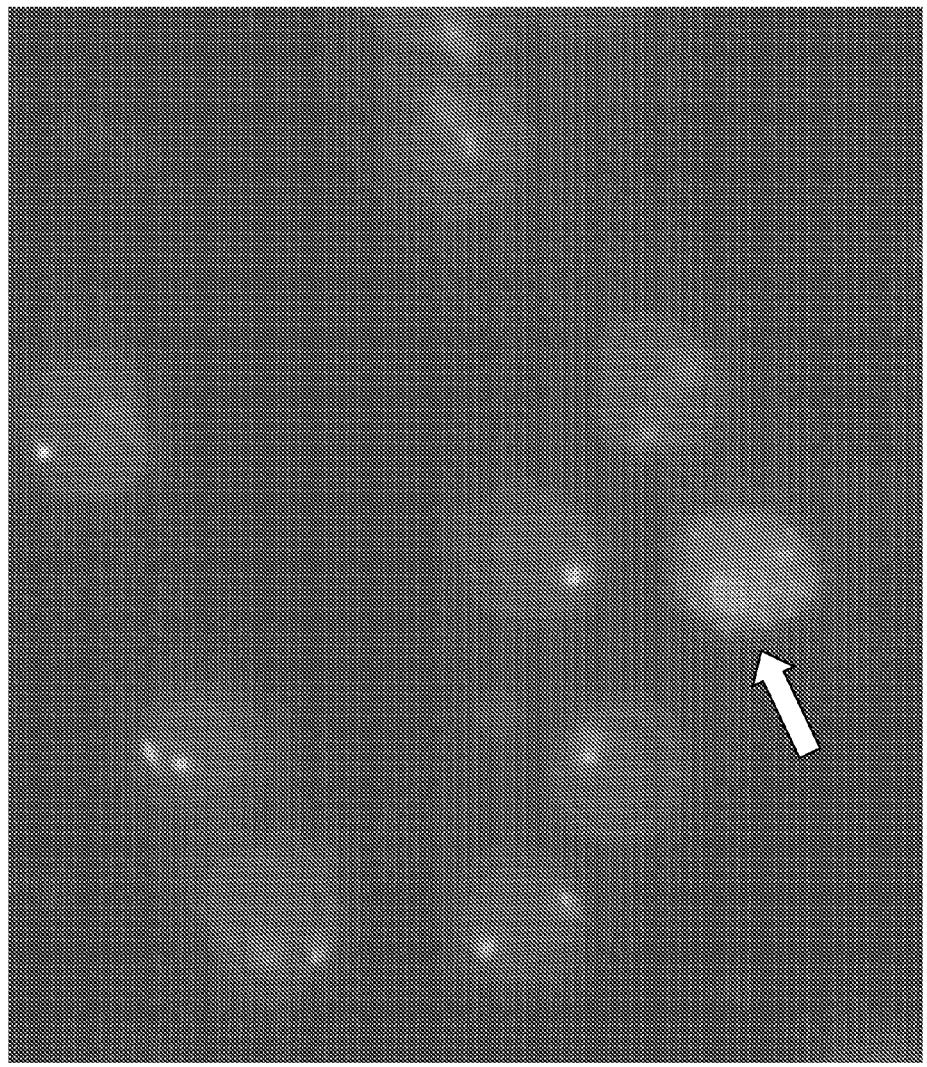
FIG. 5. Fetal cell showing vimentin staining. The arrow indicates the fetal cell.

The fetal origin of cells enriched by magnetic cell sorting (MACS) with the CD105 protocol was tested in 32 blood samples from pregnant women carrying male fetuses. FISH was carried out with X- and Y-chromosome specific probes, and cells that exhibited one X and one Y signal significantly bigger than the X signal were considered fetal cells (FIG. 1). Between 0.1 and 1.1 fetal cells per ml of blood were detected in maternal blood samples (FIG. 2). 97% of the samples were positive for fetal cells. In one blood sample no fetal cells were detected.

Twenty-one male fetal cells were characterized by staining with anti-cytokeratin 7, anti-pan cytokeratin and anti-vimentin antibodies using the protocol described above. Three of 21 fetal cells stained positive with the anti-cytokeratin 7 antibody, 10 of 14 cytokeratin 7 negative cells stained positive with the anti-pan cytokeratin antibody, while 3 out of 4 fetal cells negative for cytokeratin staining stained positive with the anti-vimentin antibody. In addition, 4 out of 4 pan cytokeratin positive cells also showed positive staining with the anti-vimentin antibody. These results demonstrate, that CD105 based magnetic cell sorting (MACS) of maternal blood samples reveal a novel fetal cell type in maternal blood expressing cytokeratins and/or vimentin, thus discriminating this cell type from fetal trophoblasts.

Example 2

Whole Blood Selection and Inside Column Staining

Blood Sampling

Peripheral blood samples of 30 ml were obtained from pregnant women 11 to 14 week's gestational age. Blood samples were drawn before an invasive procedure and after informed consent. All blood samples were collected in either heparinized tubes or EDTA tubes and processed within 4 hours after they were collected.

In addition to the heparin blood, 5 ml of blood was drawn into EDTA tubes. This blood was used for fetal gender analysis. The gender of the fetus was determined by real time PCR of free fetal DNA using γ-chromosome specific genes.

Preparation of Blood Samples—CD105 Selection 20-50 μl of CD105 microbeads (Miltenyi) were added per ml of blood, and after mixing the sample was incubated for 30 minutes at room temperature. After incubation, the blood sample was aliquoted into 6 pre-coated 50 ml tubes (pre-coating buffer was 2% BSA in PBS w/o Ca2+ and Mg2+) and 20 ml of MACS-buffer was added to each tube prior to centrifugation at 445 g for 12 minutes at 4° C. The supernatants were removed and MACS-buffer was added to a final volume of 7.5 ml. After careful mixing using a pre-coated pipette the CD105 labelled whole blood was applied to 2 pre-washed whole blood columns in aliquots of 3 ml of blood. When the blood had run through the columns, the columns were washed twice with 4 ml MACS-buffer, removed from the magnet and placed on a pre-coated 15 ml tube, and the cells were eluted from the columns by plunging using 5 ml of whole blood column elution buffer (Miltenyi). After centrifugation at 445 g for 12 minutes at 4° C. the supernatant was discarded and the cell pellet was re-suspended in 500 μl of PBS using a pre-coated pipettetip.

Fixation and Permeabilization

The cells were fixed for 20 minutes after adding 500 μl of inside fix (Miltenyi) After fixation, 10 ml of MACS-buffer was added and the tubes were centrifuged at 500 g for 10 minutes at 4° C. The supernatant were then discarded and the cell pellet was re-suspended in 500 µl of MACS-buffer. The cells were permeabilized 500 µl of ice-cold MeOH and incubated for 10 minutes at 4° C. The cells were then applied to a pre-washed MS column (Miltenyi) already placed in the magnet. After the cell suspension had entered the column completely, the cells were washed by applying 500 µl of MACS-buffer to the column.

Staining of Cells Inside MS Columns.

Fetal cells were stained with a cocktail of the following antibodies. Pan Cytokeratin (product no. C2562, Sigma-Aldrich). Cytokeratin 7 (product no. M7018, DAKO Cytomation) and Cytokeratin 8/18 (product 18.0213, Invitrogen). The anti-pan cytokeratin antibody recognizes human cytokeratin 1, 4-6, 8, 10, 13, 18 and 19. The anti-cytokeratin 7 antibody recognizes human cytokeratin 7, and the anti-cytokeratin 8/18 recognizes cytokeratin 8/18. All three antibodies are mouse monoclonals isotype IgG1, IgG2.

Before antibody staining, columns were pre-incubated for 10 minutes at room temperature after having applied 500 µl Imaging Enhancer (Molecular Probes) and then washed once by applying 500 µl of MACS-buffer. Columns were then incubated for 30 minutes at room temperature after having applied 200 µl of the cytokeratin cocktail diluted 1:50 in blocking buffer consisting of 4×SSC containing 10% normal goat serum, 1% BSA and 0.5% blocking reagent (Roche). After antibody incubation, columns were washed 3 times with 500 µl of MACS-buffer. For detection, columns were incubated for 30 minutes at room temperature with 200 µl AlexaFluor-488 conjugated F(ab)2 fragments of goat anti-mouse IgG (Invitrogen) diluted 1:50 in blocking buffer, washed 3 times with 500 µl MACS-buffer and then incubated for 30 minutes at room temperature with 200 µl AlexaFluor-488 conjugated F(ab)2 fragments rabbit anti-goat IgG (Invitrogen) diluted 1:50 in blocking buffer. After incubation, the columns were then washed once with 500 µl MACS-buffer and twice with 500 µl PBS w/o Ca2+ and Mg2+. The columns were then transferred from the magnet to a 15 ml tube and the cells were recovered by applying 500 µl MACS-buffer twice using the plunger when applying MACS-buffer the second time. After the cells have been pelleted by centrifugation at 500 g for 10 minutes at 4° C., the cellpellet is re-suspended in PBS w/o Ca2+ and Mg2+, the cells were smeared onto slides and the slides were air-dried overnight in the dark and then mounted in Vectashield with DAPI (Vector Laboratories).

Analysis of Cytokeratin Stained Slides

Identification of Cytokeratin Stained Cells

Fetal cells stained with the anti-cytokeratin antibody cocktail were identified by automatic scanning using the MetaCyte scanning system developed by Metasystems. Slides were scanned at 10× magnification using a classifier developed and optimized in-house for detection of cytokeratin stained cells. After scanning, cells identified by the scanners were inspected visually by automatic re-location.

FISH Identification/Verification of (Male) Fetal Cells

In case of male pregnancies, the specificity of the antibody staining was confirmed by XY FISH. Before hybridization, the cover slips were removed and the slides were rinsed in PBS for 5 minutes and then dehydrated for 3 minutes each in 60%, 80% and 99.9% ethanol. The chromosome-specific repeat DXZ1 probe CEP X alpha satellite DNA labelled with spectrum aqua and DYZ1 probe CEP Y satellite III labelled with spectrum orange (Abbott Molecular) were used for this analysis. Hybridization mixtures containing both probes were prepared by mixing 1 part of the X-probe, 1 part of the Y-probe, 1 part of distilled water and 7 parts of hybridization buffer. Fifteen µl of hybridization mixture were added and covered by a 24×24 mm cover slip. The cover slips were sealed with rubber cement, and the DNAs denatured on a hot plate at 83.5° C. for 7 minutes and hybridized overnight in a humidified atmosphere at 42° C. Hybridized slides were washed for 2 minutes at 73 C in 0.4×SSC with 0.3% Tween 20 and for 1 minute at room temperature in 2×SSC with 0.1% Tween 20. The slides were then mounted in Vectashield with DAPI.

Trisomi 21 Analysis

In case of high risk pregnancies (1:50 or higher), cytokeratin stained fetal cells were analysed for the presence or absence of trisomi 21 (Downs syndrome) using the chromosome 21 specific LSI 21 probe labelled in spectrum orange (Abbott Molecular). The CEP X probe labelled in spectrum aqua was used together with the LSI 21 probe as an internal control. Hybridization mixtures containing both probes were prepared by mixing 1 part of the X-probe, 1 part of the LSI 21 probe, 1 part of distilled water and 7 parts of hybridization buffer.

Figure 6:
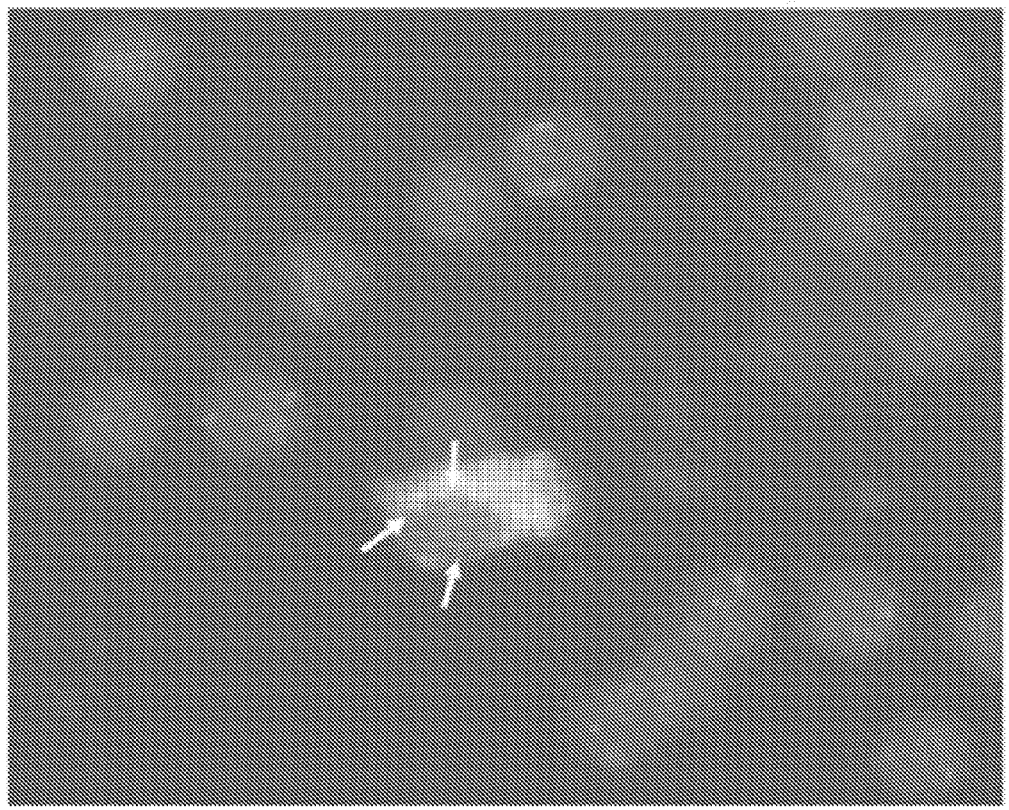
FIG. 6. Fetal cell stained with cytokeratin (green) and with FISH probes for chromosome 21 (red) and the X chromosome (blue). Arrows point to the three copies of chromosome 21 in the fetal cell. The background of maternal cells contains two copies each of chromosome 21

Before FISH, the cover slips were removed by washing the slide for 10 minutes in 2% paraformaldehyde (PFA) in PBS. The slides were then post-fixed by incubation for 10 minutes in 4% PFA, washed in PBS for 2 minutes and dehydrated for 3 minutes each in 60%, 80% and 99.9% EtOH. After air-drying the slides were pre-denatured with hybridization mixture containing no probes in the following way. 18 µl hybridization mixture was added and covered with a 24×24 mm cover slip. The slides were then placed on a hot plate at 90° C. for 10 minutes. The cover slips were removed, the slides were washed in PBS for 5 minutes and in ice-cold 99.9% EtOH for 10 minutes. After air drying 18 µl hybridization mixture containing the LSI 21 probe and CEP X probe was added and covered with a 24×24 mm cover slip. The cover slip was sealed with rubber cement, and the DNAs were denatured on a hot plate at 90° C. for 10 minutes and hybridized overnight in a humidified atmosphere at 42° C. Hybridized slides were washed for 2 minutes at 73° C. in 0.4×SSC with 0.3% Tween 20 and for 1 minute at room temperature in 2×SSC with 0.1% Tween 20. The slides were then mounted in Vectashield with DAPI. Enumeration of chromosome 21 FISH signals in stained fetal cells was done by re-location using the original scan file. FIG. 6 *shows* a case of non-invasive prenatal diagnosis of trisomi 21 (Downs syndrome).

The invention claimed is:

1. A method of detecting cells having a combined endothelial-epithelial phenotype, said method comprising the steps of:
   a) providing a blood sample from a pregnant woman, or a fraction thereof;
   b) contacting the sample or a fraction thereof with a hybridization probe comprising at least 10 contiguous nucleotides complementary to a gene encoding an endothelial cell marker or a ligand directed to an endothelial cell marker, wherein said endothelial cell marker is selected from the group consisting of CD105, CD146, CD141, vimentin, VCAM, ICAM, VEGFR-1, VEGFR-2, VEGFR-3, ITGA5, ITGB5, CDH11, and CDH3;
   c) selecting the cells expressing said endothelial cell marker, thereby obtaining a population of cells enriched in cells expressing said endothelial cell marker;
   d) contacting the enriched population of cells with a hybridization probe comprising at least 10 contiguous nucleotides complementary to a gene encoding an epithelial cell marker or a ligand directed to an epithelial cell marker, wherein said epithelial cell marker is selected from the group consisting of CK1, CK2, CK3, CK4, CK5, CK6, CK7, CK8, CK9, CK10, CK13, CK14, CK15, CK16, CK17, CK18, and CK19; and
   e) detecting cells expressing said epithelial cell marker in the cells obtained in step d as having a combined endothelial-epithelial phenotype.

2. The method of claim 1, wherein the target of the endothelial marker ligand is located at the surface of the detected cells.

3. The method of claim 1, wherein the target of the epithelial marker hybridization probe and/or ligand is located at an intracellular location of the detected cells.

4. The method of claim 1, wherein the blood sample is whole blood.

5. The method of claim 1, further comprising subjecting the cells obtained in step c) to fixation.

6. The method of claim 5, further comprising subjecting the fixed cells to permeabilization before being contacted with the epithelial cell marker directed ligand or hybridization probe.

7. The method of claim 1, wherein the endothelial cell marker is selected from the group consisting of: CD105, CD146 and CD141.

8. The method of claim 7, wherein the endothelial cell marker is CD105.

9. The method of claim 1, wherein the epithelial cell marker is selected from the group consisting of: CK8, CK18, CK19 and CK7.

10. The method of claim 1 further comprising contacting the sample with M30 antibody.

11. The method of claim 1, further comprising isolating one or more cells having endothelial-epithelial phenotype.

12. The method of claim 1, wherein the step of detecting comprises a method selected from the group consisting of fluorescent in situ hybridization (FISH), northern blotting, southern blotting, DNA/RNA sequencing, microarray analysis, and amplification.

13. The method according to claim 1 wherein the selection of cells expressing the endothelial cell marker in step b) is performed by immunomagnetic separation using ligands coupled to magnetic beads, wherein the cells are loaded onto an immunomagnetic cell sorting system and cells expressing the endothelial cell marker interacting with magnetic bead-coupled ligands are retained by the immunomagnetic cell sorting system.

14. The method according to claim 13, wherein the retained cells are subsequently released from the immunomagnetic cell sorting system and brought in contact with an epithelial cell marker ligand.

15. The method according to claim 1, wherein the selection of cells expressing the endothelial cell marker is performed by immobilized antibody selection, wherein the blood sample or fraction thereof is brought in contact with an immobilized ligand directed to an endothelial cell marker in a flow system.

16. The method according to claim 1 wherein the selection of cells expressing the epithelial cell marker in step b) is performed by immunomagnetic separation using ligands coupled to magnetic beads, wherein the cells are loaded onto an immunomagnetic cell sorting system and cells expressing the epithelial cell marker interacting with magnetic bead-coupled ligands are retained by the immunomagnetic cell sorting system.

17. The method according to claim 16, wherein the retained cells are subsequently released from the immunomagnetic cell sorting system and brought in contact with an endothelial cell marker ligand.

18. A method of selecting cells having an endothelial-epithelial phenotype, the method comprising the steps of:
   a) providing a blood sample from a pregnant woman, or a fraction thereof;
   b) contacting the sample or a fraction thereof with a hybridization probe comprising at least 10 contiguous nucleotides complementary to a gene encoding an epithelial cell marker or a ligand directed to an epithelial cell marker, wherein said epithelial cell marker is selected from the group consisting of CK1, CK2, CK3, CK4, CK5, CK6, CK7, CK8, CK9, CK10, CK13, CK14, CK15, CK16, CK17, CK18, and CK19;
   c) contacting the sample or a fraction thereof with a hybridization probe comprising at least 10 contiguous nucleotides complementary to a gene encoding an endothelial cell marker or a ligand directed to an endothelial cell marker, wherein said endothelial cell marker is selected from the group consisting of CD105, CD146, CD141, vimentin, VCAM, ICAM, VEGFR-1, VEGFR-2, VEGFR-3, ITGA5, ITGB5, CDH11, and CDH3; and d) selecting cells expressing said epithelial cell marker and said endothelial cell marker, thereby obtaining a population of cells enriched with a combined endothelial-epithelial cell phenotype.

19. The method of claim 18, wherein the target of the endothelial marker ligand is located at the surface of the cell to be identified.

20. The method of claim 18, wherein the target of the epithelial marker hybridization probe is located at an intracellular location of the cell to be identified.

21. The method of claim 18, wherein the blood sample is whole blood.

22. The method of claim 18, further comprising subjecting the cells obtained in step c) to fixation.

23. The method of claim 22, further comprising subjecting the fixed cells to permeabilization before being contacted with the epithelial cell marker directed ligand or hybridization probe.

24. The method of claim 18, wherein the endothelial cell marker is selected from the group consisting of: CD105, CD146, and CD141.

25. The method of claim 24, wherein the endothelial cell marker is CD105.

26. The method of claim 18, wherein the epithelial cell marker is selected from the group consisting of: CK7, CK8, CK18, and CK19.

27. The method of claim 18 further comprising contacting the sample with M30 antibody.

28. The method of claim 18, further comprising isolating one or more cells having endothelial-epithelial phenotype.

29. The method of claim 18, wherein the step of detecting comprises a method selected from the group consisting of fluorescent in situ hybridization (FISH), northern blotting, southern blotting, DNA/RNA sequencing, microarray analysis, and amplification.

30. The method according to claim 18, wherein the selection of cells expressing the epithelial cell marker is performed by immobilized antibody selection, wherein the blood sample or fraction thereof is brought in contact with an immobilized ligand directed to an epithelial cell marker in a flow system.

* * * * *